United States Patent
Malhotra et al.

(10) Patent No.: US 10,933,047 B2
(45) Date of Patent: Mar. 2, 2021

(54) STABILIZED CABAZITAXEL FORMULATIONS

(71) Applicant: Cipla Limited, Mumbai (IN)

(72) Inventors: Geena Malhotra, Mumbai (IN); Sarabjit Singh, Maharashtra (IN); Ravichandra Bhadravathi Vedamurthy, Maharashtra (IN); Anirban Mallik Thakur, Maharashtra (IN); Dhiraj Abhyankar, Maharashtra (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 15/846,841

(22) Filed: Dec. 19, 2017

(65) Prior Publication Data

US 2018/0104212 A1    Apr. 19, 2018

Related U.S. Application Data

(62) Division of application No. 15/342,457, filed on Nov. 3, 2016, now Pat. No. 10,188,626.

(30) Foreign Application Priority Data

Nov. 3, 2015 (IN) .......................... 4179/MUM/2015
Jun. 3, 2016 (IN) ............................. 2016/21019165

(51) Int. Cl.
| | | |
|---|---|---|
| A61K 47/14 | (2017.01) | |
| A61K 47/42 | (2017.01) | |
| A61K 47/10 | (2017.01) | |
| A61K 47/12 | (2006.01) | |
| A61K 31/337 | (2006.01) | |
| A61K 9/00 | (2006.01) | |

(52) U.S. Cl.
CPC .......... *A61K 31/337* (2013.01); *A61K 9/0019* (2013.01); *A61K 47/10* (2013.01); *A61K 47/12* (2013.01); *A61K 47/14* (2013.01); *A61K 47/42* (2013.01)

(58) Field of Classification Search
CPC ........ A61K 47/10; A61K 47/12; A61K 47/42; A61K 47/14; A61K 31/337; A61K 9/00
See application file for complete search history.

(56) References Cited

U.S. PATENT DOCUMENTS

| | | |
|---|---|---|
| 5,403,858 A | 4/1995 | Bastart et al. |
| 5,438,072 A | 8/1995 | Bobee et al. |
| 5,698,582 A | 12/1997 | Bastart et al. |
| 5,714,512 A | 2/1998 | Bastart et al. |
| 5,750,561 A | 5/1998 | Bastart et al. |
| 5,847,170 A | 12/1998 | Bouchard et al. |
| 7,241,907 B2 | 7/2007 | Didier et al. |
| 2010/0267817 A1 | 10/2010 | Jang et al. |
| 2010/0305202 A1 | 12/2010 | Hwang et al. |
| 2011/0118354 A1 | 5/2011 | Carter et al. |
| 2011/0130446 A1 | 6/2011 | Parente Duena et al. |
| 2012/0065255 A1 | 3/2012 | Palepu et al. |
| 2013/0202659 A1* | 8/2013 | Crawford ............... A61K 47/60 424/400 |
| 2017/0087121 A1* | 3/2017 | Chan .................... A61K 9/0053 |
| 2018/0085339 A1 | 3/2018 | Malhotra et al. |

FOREIGN PATENT DOCUMENTS

| | | |
|---|---|---|
| CN | 104887626 A | 9/2015 |
| WO | 2007020085 A2 | 2/2007 |
| WO | 2009115655 A2 | 9/2009 |
| WO | 2010023321 A1 | 3/2010 |
| WO | 2013024495 A1 | 2/2013 |
| WO | 2016113752 | 7/2016 |

OTHER PUBLICATIONS

Villanueva et al., 2011, caplus an 2011:415562.*
Galsky et al., 2010, caplus an 2010:1101273.*
Ansari et al., 2011, caplus an 2011:536403.*
Wan et al., 2018, caplus an 2018:2131674.*
Dizerega, 2018, caplus an 2018:1741423.*
Bteich et al., 2018, caplus an 2018:898072.*
Schmalenberg et al., 2018, caplus an 2018:23622.*
Joshi et al., 2017, caplus an 2017:1751471.*
Jetvana, 2017, http://www.guildlink.com.au/gc/ws/sw/pi.cfm?product=swpjevta21017.*
KolliphorHS15, 2019, https://www.sigmaaldrich.com/catalog/product/sigma/42966?lang=en&region=US.*
CN102232933 machine translation, published Nov. 2011, translated 2019.*
Non-Final Office Action issued in U.S. Appl. No. 15/342,457, dated Sep. 1, 2017.
Solutol, 2017, https://pubchem.ncbi.nlm.nih.gov/compound/71311956#section=Synonymns.
Nieuweboer, et al., "Influence of Drug Formulation on OATP1B—Mediated Transport of Paclitaxel", Cancer Research 71:11, 2014, 3137-3145.
Non-Final Office Action issued in U.S. Appl. No. 15/342,457, dated May 10, 2018.

* cited by examiner

*Primary Examiner* — Sun Jae Yoo
(74) *Attorney, Agent, or Firm* — Meunier Carlin & Curfman LLC

(57) ABSTRACT

Disclosed herein are improved formulations for the cabazitaxel. The formulations exhibit increased storage stability relative to other formulations, and are simpler for health care providers to prepare and administer to patients.

19 Claims, 6 Drawing Sheets

| Over Night Stand | Commercial Formulation | | RTD Test Formulation | |
|---|---|---|---|---|
| | 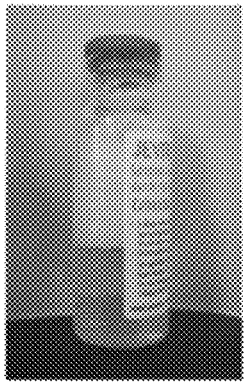 | 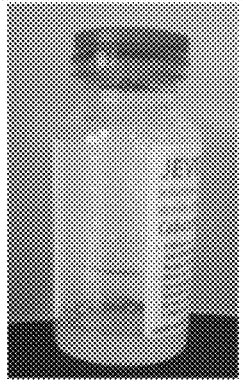 | 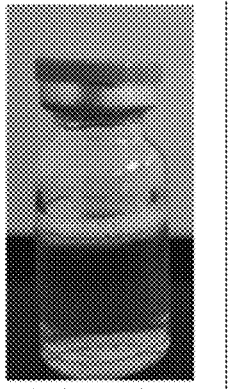 | 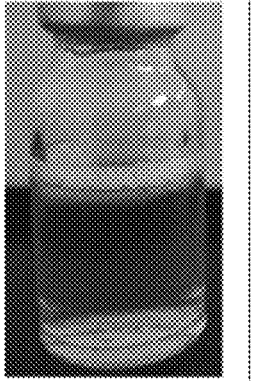 |
| | Dilution (0 hr) | After 4 hr | Dilution (0 hr) | After 15 hr |
| | Commercial reconstituted formulation | | RTD formulation reconstituted with 5 % dextrose solution | |

FIGURE 3

| Over Night Stand | Commercial Formulation | | RTU Test Formulation | |
|---|---|---|---|---|
| | 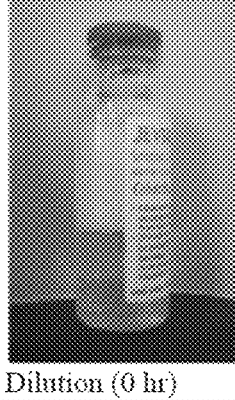 | 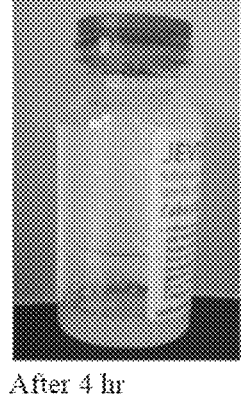 | 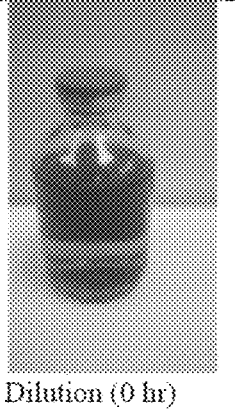 | 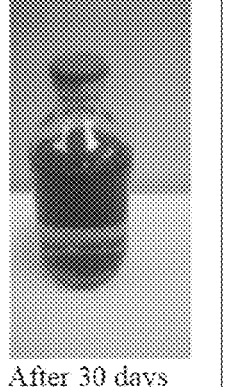 |
| | Dilution (0 hr) | After 4 hr | Dilution (0 hr) | After 30 days |
| | Commercial reconstituted formulation | | RTU formulation comprising albumin solution | |

FIGURE 4

STABILIZED CABAZITAXEL FORMULATIONS

CROSS REFERENCE TO RELATED APPLICATION

This application is a divisional of U.S. application Ser. No. 15,342,457, filed on Nov. 3, 2016 and claims the benefit of Indian Application 4179/MUM/2015, filed on Nov. 3, 2015, and Indian Provisional Application 2016/21019165, filed on Jun. 3, 2016, the contents of each are hereby incorporated in their entirety.

FIELD OF THE INVENTION

The present invention relates to pharmaceutical formulation comprising cabazitaxel in the form of ready-to-dilute and/or ready-to-use solutions or concentrates. Another aspects relate to stable injectable formulations of cabazitaxel ready for direct dilution with infusion solution, without any need for preparation of premix solutions, and manufacturing processes thereof.

BACKGROUND

Cabazitaxel is the active ingredient in the product JEVTANA® Injection 60 mg/1.5 mL, sold by Sanofi Aventis as a sterile, non-pyrogenic, clear yellow to brownish-yellow viscous solution in single-use vials containing 60 mg cabazitaxel (calculated on an anhydrous and solvent free basis) and 1.56 g of polysorbate 80. Each mL contains 40 mg cabazitaxel (anhydrous) and 1.04 g polysorbate 80. JEVTANA® Injection is a micellar formulation.

Cabazitaxel shows polymorphism and the polymorphic form A of an acetone solvate is known to offer manufacturing feasibility, reproducibility, and stability as reported in art.

The JEVTANA® product requires two dilutions prior to intravenous infusion. The first dilution produces a composition of approximately 4.5 mL clear, colorless, sterile, and non-pyrogenic solution containing 13% (w/w) ethanol in water. This pre-mix solution is supersaturated by about 400% (10 mg cabazitaxel/mL) is inherently physically unstable. It requires repeated inversions for at least 45 seconds to assure complete mixing of the concentrated drug solution and the diluent. The pre-mix solution must be used immediately and requires further dilution before administration. A volume of premix solution calculated based on a dose of 25 mg/m$^2$ is withdrawn and injected into a PVC-free container of either 0.9% sodium chloride solution or 5% dextrose solution for infusion. After this second dilution, the concentration of cabazitaxel in the infusion solution should be between 0.10 mg/mL and 0.26 mg/mL. The diluted infusion solution should be used for intravenous administration immediately, within 8 hours, if stored at room temperature, or within 24 hours, if stored under refrigerated conditions, including the 1-hour infusion period. Because of the serial dilutions required, there is a chance that an incorrect final dosage form will be prepared. Severe complications can result from overdose, which may include exacerbation of the adverse reactions, sometimes leading to fatal outcomes. The most common serious adverse events with cabazitaxel chemotherapy included myelosuppression (i.e., anaemia, neutropenia, leukopenia, and thrombocytopenia), hypersensitivity reactions, fatigue, diarrhea, peripheral neuropathy, back pain, and arthralgia and also potential GI symptoms, such as nausea, vomiting, and diarrhea and renal failure.

JEVTANA® (cabazitaxel injection 60 mg/1.5 mL) comprises of polysorbate 80 as a primary solubilizing vehicle. However, based on the published literature, polysorbate 80 is known to induce hypersensitivity reactions.

Apart from the reconstitution errors associated with JEVTANA® causing exacerbation of adverse events, this two-step dilution process is cumbersome and time consuming. In addition, complications like drug crystallization and possibilities of needle stick injuries and contamination during dilution are also concerns. As both the pre-mix solution and the second diluted infusion solution are supersaturated, the solutions may crystallize over time. If crystals and/or particulates appear in the diluted infusion solution, the formulation is ruined, may not be used, and must be thrown away.

There remains a need for improved formulations of cabazitaxel having improved ease of manufacture, means of administration, and stability over time. There remains a need for formulations which are easy for healthcare providers to prepare and administer. There remains a need for cabazitaxel formulation having improved stability over time, especially when stored under ambient conditions.

It is an object of the invention to provide stabilized, ready-to-dilute, cabazitaxel formulations.

It is another object of the invention to provide stabilized, ready-to-use, cabazitaxel formulations.

It is another object of the invention to provide a process for preparing stabilized, ready-to-dilute, cabazitaxel formulations.

It is another object of the invention to provide a process for preparing stabilized, ready-to-use, cabazitaxel formulations.

It is another object of the present invention to provide safe, efficacious and easy to use formulations of cabazitaxel.

It is another object of the present invention to provide methods for treating patients with hormone-refractory metastatic prostate cancer previously treated with a docetaxel-containing treatment regimen in combination with prednisone by administering stable ready-to-dilute/ready-to-use parenteral formulations of cabazitaxel.

SUMMARY

According to an aspect of the present invention, there is provided pharmaceutical formulations comprising cabazitaxel or its pharmaceutically acceptable salts, hydrates, solvates, metabolites, polymorphs, and mixtures thereof In some embodiments, the formulations are in the form of ready-to-dilute and/or ready-to-use solutions or concentrates. Further aspects relate to stable injectable formulations of cabazitaxel ready for direct dilution with infusion solution, without any need for preparation of premix solutions, and manufacturing processes thereof.

According to another aspect of the present invention, there is provided single vial formulations of cabazitaxel, ready for dilution direct dilution with infusion solution.

According to another aspect of present invention, there is provided cabazitaxel ready-to-dilute formulations comprising macrogol 15 hydroxystearate.

According to another aspect of present invention, there is provided cabazitaxel ready-to-dilute formulation comprising caprylocaproyl polyoxylglycerides.

According to another aspect of present invention, there is provided cabazitaxel ready-to-dilute formulations comprising diethylene glycol monoethyl ether.

Another object of the present invention is to provide ready-to-use cabazitaxel formulations comprising macrogol 15 hydroxystearate.

Another object of the present invention is to provide cabazitaxel ready-to-use formulations comprising caprylocaproyl polyoxylglycerides.

Another object of present invention is to provide cabazitaxel ready-to-use formulations comprising diethylene glycol monoethyl ether.

Yet another object of the present invention is to provide ready-to-use cabazitaxel formulations comprising albumin solution.

According to another aspect of the present invention, there is provided single vial formulations of cabazitaxel, ready for direct introduction into an infusion bag or direct dilution with infusion solution.

According to another aspect of present invention, there is provided processes for preparation of ready-to-dilute cabazitaxel formulations.

According to another aspect of the present invention, there is provided processes for preparation of ready-to-use formulations.

According to another aspect of the present invention, there is provided a method for treating patients with hormone-refractory metastatic prostate cancer previously treated with a docetaxel-containing treatment regimen in combination with prednisone by administering stable ready-to-dilute and/ or ready-to-use parenteral formulation of cabazitaxel The details of one or more embodiments are set forth in the descriptions below. Other features, objects, and advantages will be apparent from the description and from the claims.

BRIEF DESCRIPTION OF THE FIGURES

FIG. 3: Visual characterization of commercial formulation vs RTD test formulation FIG. 4: Visual Characterization of commercial Formulation vs RTU Test Formulation

DETAILED DESCRIPTION

Figure 1:
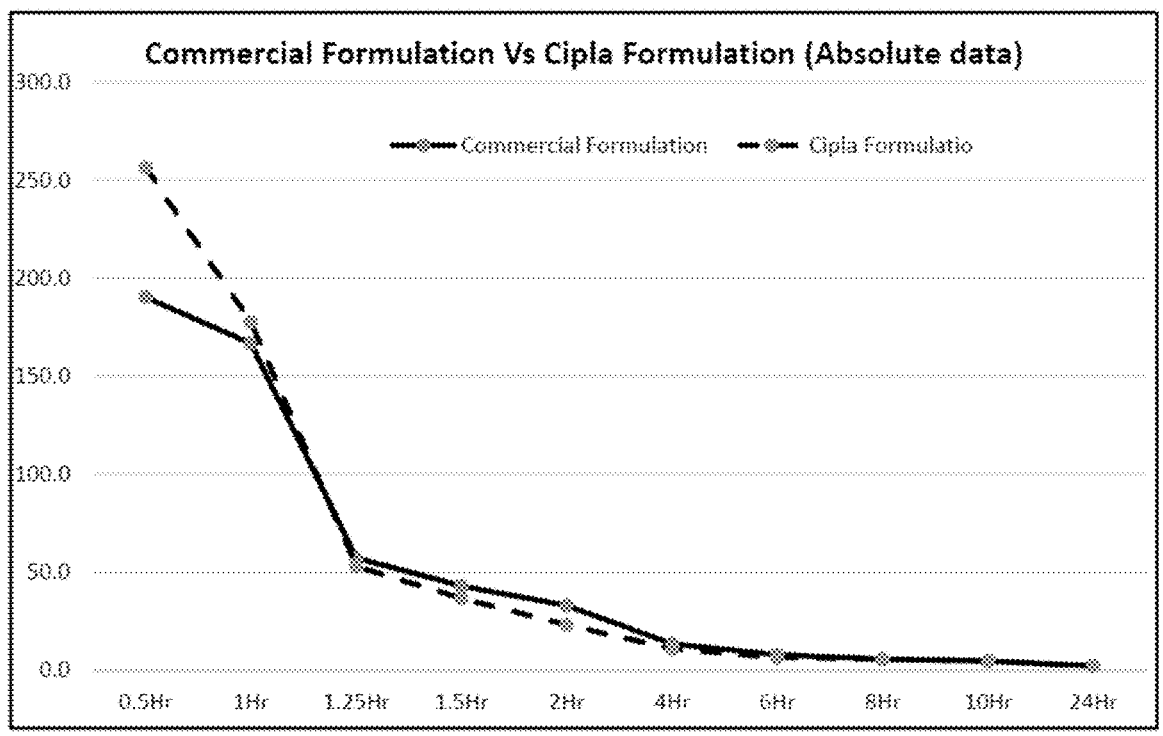
FIG. 1: Commercial formulation vs test formulation plasma concentration absolute data.
Figure 2:
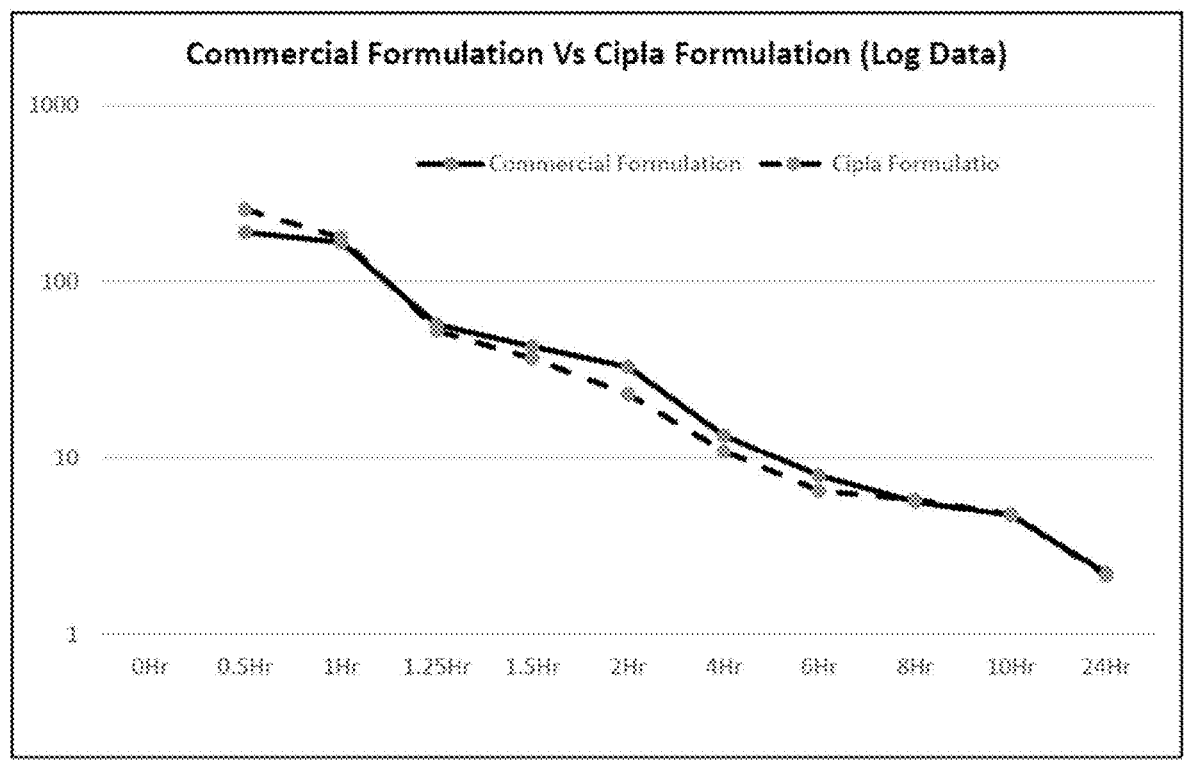
FIG. 2: Commercial formulation vs test formulation plasma concentration log data
Figure 5:
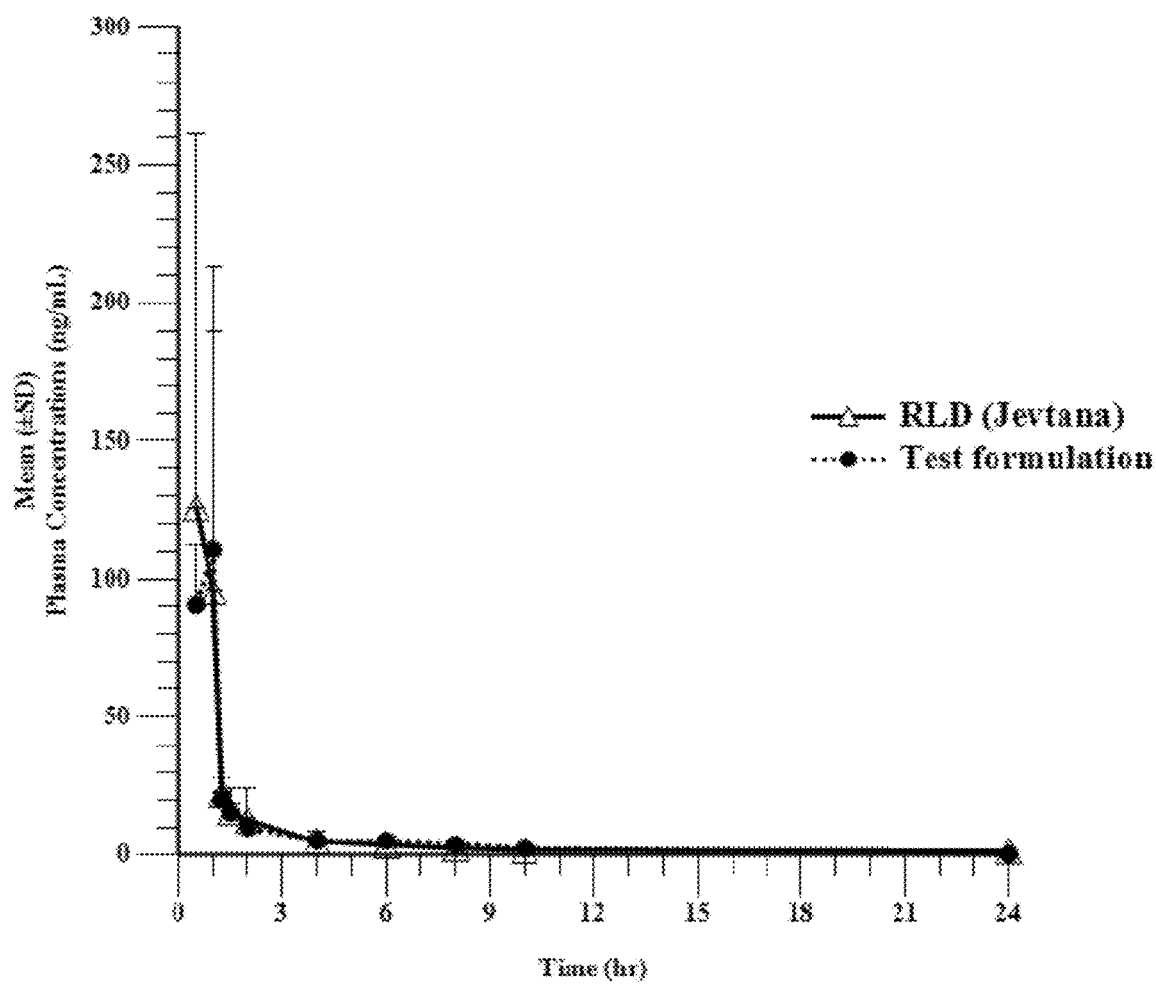
FIG. 5: Plasma concentration of cabazitaxel (1.25 mg/kg) following intravenous (1 hour infusion) administration in male Wistar rats.
Figure 6:
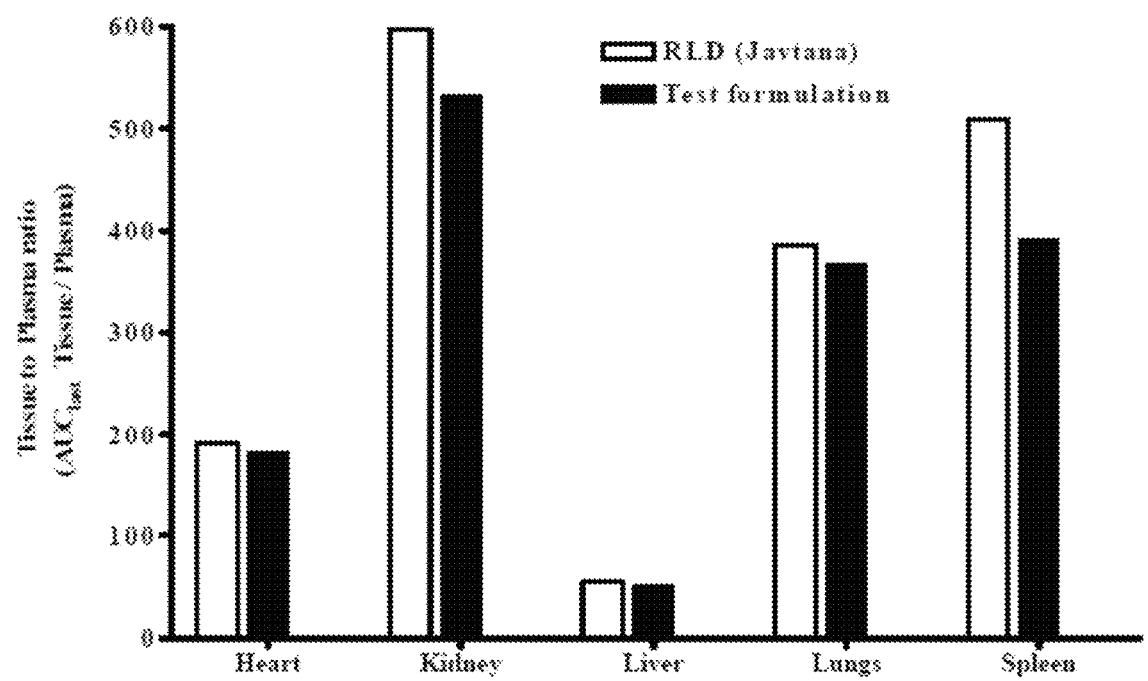
FIG. 6: Tissue vs plasma ratio for mean exposures (AU-$C_{last}$) of cabazitaxel (RLD and test formulation) at 1.25 mg/kg after intravenous (1 hour infusion) route of administration in fasted male Wistar rats
Figure 7:
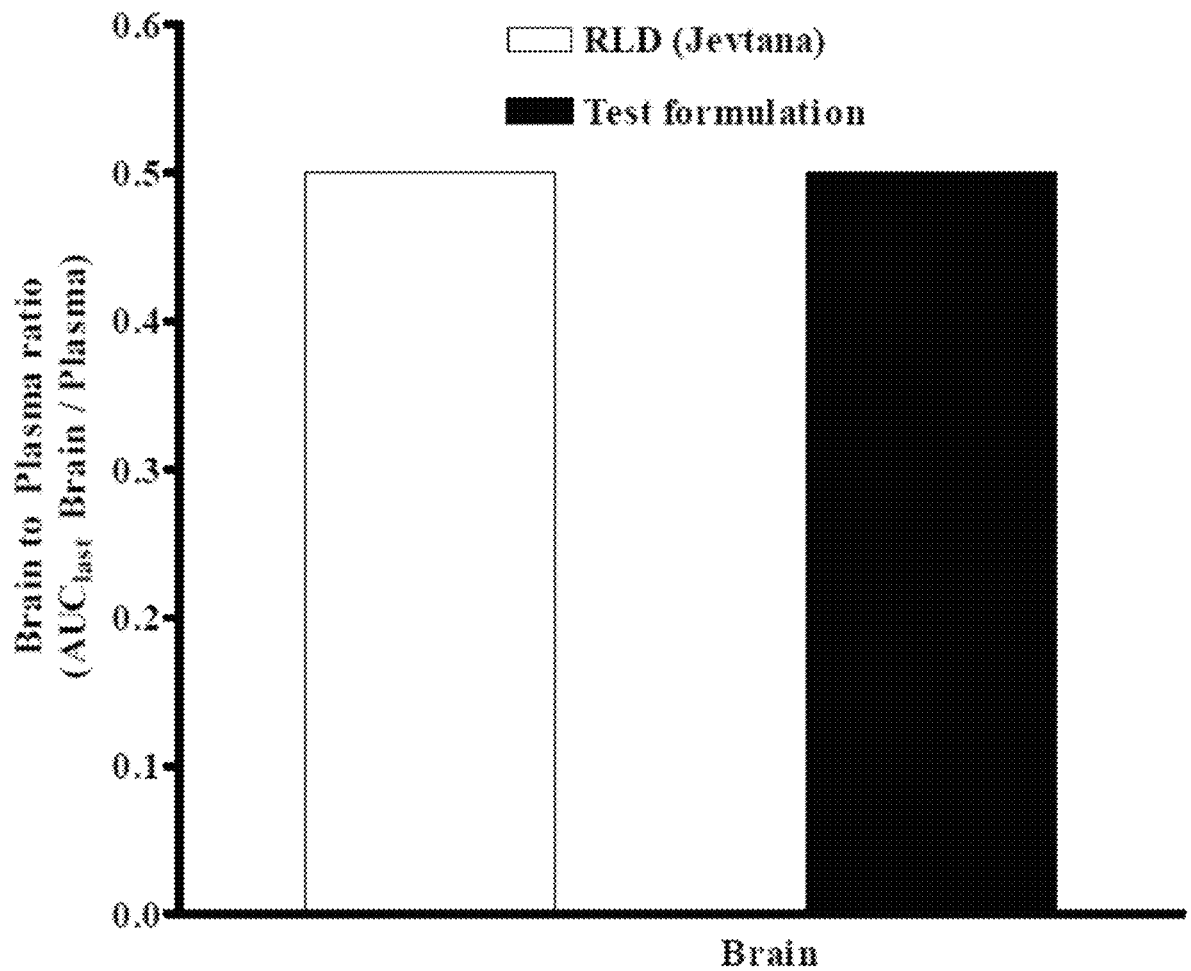
FIG. 7: Brain vs plasma ratio for mean exposures (AU-$C_{last}$) of cabazitaxel (RLD and test formulation) at 1.25 mg/kg after Intravenous (1 hour infusion) route of administration in fasted male Wistar rats
Figure 8:
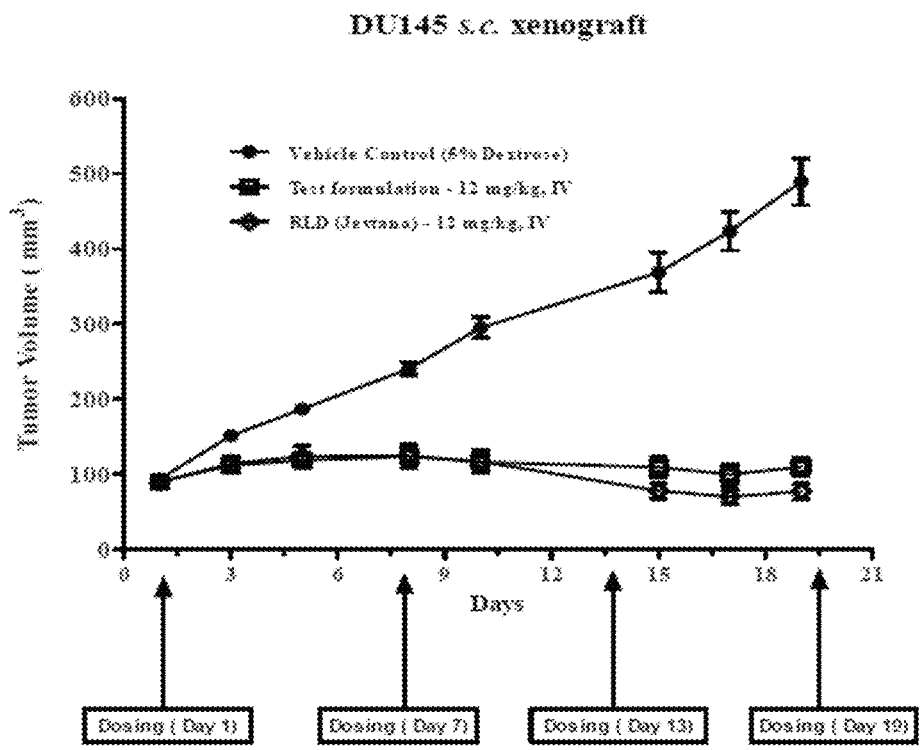
FIG. 8: Average tumor volume±SEM (mm$^3$) and percent tumor growth inhibition.
Figure 9:
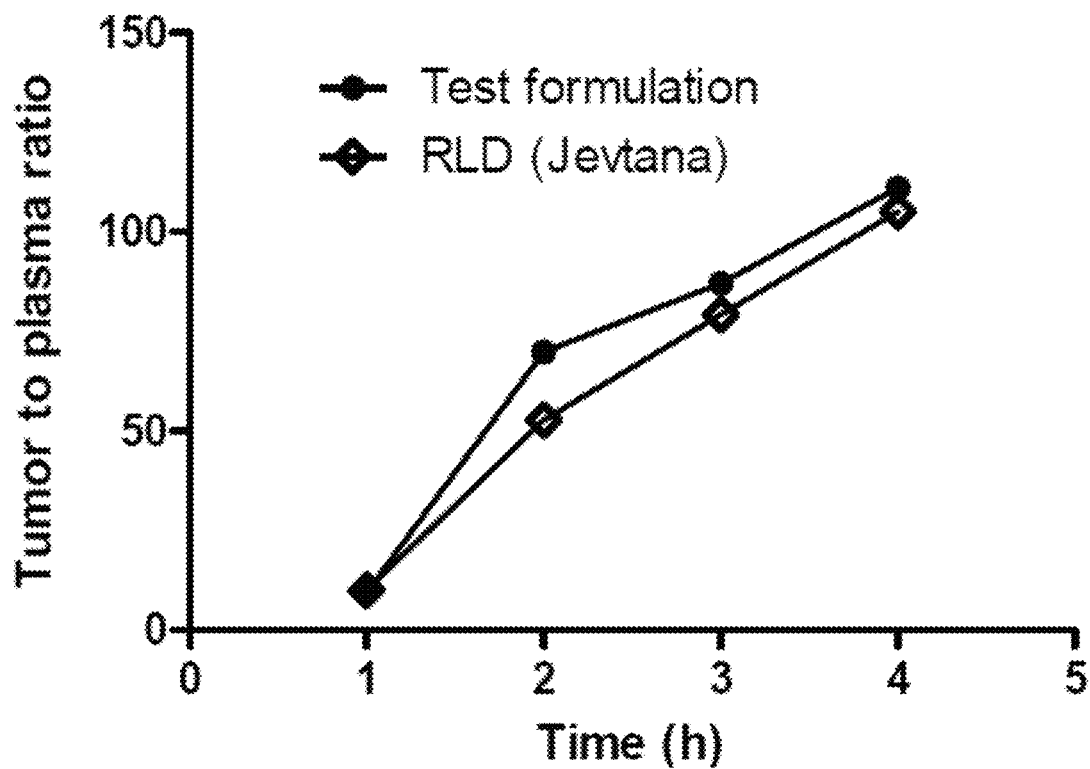
FIG. 9: Tumor to plasma ratio of cabazitaxel

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Aspects of the present application relate to pharmaceutical formulations comprising cabazitaxel, or its pharmaceutically acceptable salts, isomers, racemates, enantiomers, hydrates, solvates, metabolites, polymorphs, and mixtures thereof, in the form of ready-to-dilute and/or ready-to-use solutions or concentrates.

The drug compound "cabazitaxel" has a chemical name (2α,5β,7β,10β,13a)-4-acetoxy-13-({(2R,3S)-3[(tertbutoxycarbonyl)amino]-2-hydroxy-3-phenylpropanoyl}-oxy)-1-hydroxy-7,10-dimethoxy-9-oxo-5,20-epoxytax-11-en-2-yl benzoate and its structural formula is shown below.

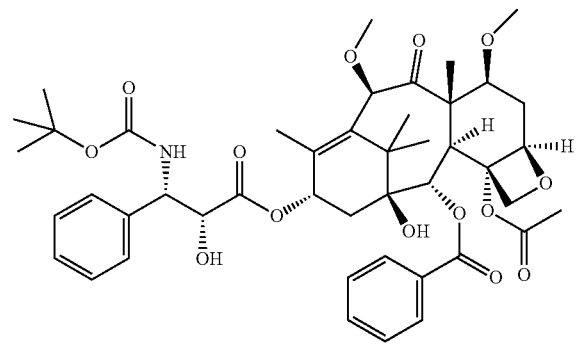

Cabazitaxel has the empirical formula of $C_{45}H_{57}NO_{14}$ and has molecular weight of 853.95. Cabazitaxel is a white to off-white powder. It is lipophilic, practically insoluble in water, having solubility about 8 pg/mL, and is soluble in alcohol.

Cabazitaxel is the 7,10-dimethoxy analogue of docetaxel, which is a member of the taxane family. It is a microtubule inhibitor, which binds to tubulin and promotes its assembly into microtubules while simultaneously inhibiting disassembly. This leads to the stabilization of microtubules, which results in the inhibition of mitotic and interphase cellular functions. It is indicated in combination with prednisone for treatment of patients with hormone-refractory metastatic prostate cancer previously treated with a docetaxel-containing treatment regimen.

Cabazitaxel is the active ingredient in product sold as JEVTANA® Injection 60 mg/1.5 mL by Sanofi Aventis as a sterile, non-pyrogenic, clear yellow to brownish-yellow viscous solution in single-use vials containing 60 mg cabazitaxel (calculated on an anhydrous and solvent free basis) and 1.56 g of polysorbate 80. Each mL contains 40 mg cabazitaxel (anhydrous) and 1.04 g polysorbate 80.

The term "cabazitaxel" is used in broad sense to include not only "cabazitaxel" per se but also its pharmaceutically acceptable salts, pharmaceutically acceptable solvates, pharmaceutically acceptable hydrates, pharmaceutically acceptable anhydrates, pharmaceutically acceptable polymorphs, pharmaceutically acceptable prodrugs, pharmaceutically acceptable tautomers, pharmaceutically acceptable complexes and the like.

The term "stable formulations" refers to any preparation of cabazitaxel having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about 2 years. As used herein, a stable formulation is one in which at least 90% of the cabazitaxel content is present after the aforementioned period of time. In some embodiments, at least 95% of the cabazitaxel content is retained after storage at 40° C./75% RH for six months. In some embodiments, at least 95% of the cabazitaxel content is retained after storage at 40° C./75% RH for three months. In some embodiments, at least 95% of the cabazitaxel content is retained after storage at 40° C./75% RH for 1 month. Cabazitaxel content can be determined using HPLC as known in the art.

Injectable formulations can be formulated as aqueous or non-aqueous solutions or suspensions. Injectable formulations can be prepared in conventional forms, either as liquid solutions or suspensions, solid forms suitable for solubilization or reconstitution or suspension in a liquid prior to injection, or as emulsions. Sterile injectable formulations can be prepared according to techniques known in the art using suitable carriers, dispersing or wetting agents, and suspending agents. The injectable formulations may be sterile injectable solutions or suspensions in a nontoxic, parenterally acceptable diluent or solvent. Among the acceptable vehicles and diluents or solvents that may be employed are water for injection, isotonic dextrose solution, Ringer's solution, isotonic sodium chloride solution, and suitable non-aqueous solvents and the like useful for parenteral administration. In addition, sterile fixed oils, fatty esters, or polyols can be employed as solvents or suspending media.

The formulations of the present application are particularly suited for use in parenteral administration, but it will be understood that the solutions may have alternative uses. Injectable formulations may be administered via any route including intramuscular, intravenous, or subcutaneous.

The formulations according to an aspect of the application may be in the form of liquid concentrates, ready-to-dilute and/or ready-to-use solutions.

The term "ready-to-dilute" refers to any preparation of cabazitaxel which are ready for dilution using dextrose solution, saline solution, or any other infusion medium for administration to patient.

The term "ready-to-use" refers to any preparation of cabazitaxel which are ready to be administered to patient directly without any further dilution or processing.

In some embodiments, the present application provides pharmaceutical formulations having cabazitaxel at concentrations about 5 mg/mL to about 200 mg/mL. For instance, the concentrations of cabazitaxel can be in the range of about 10 mg/mL to about 60 mg/mL, or about 15 mg/mL to about 50 mg/mL, or about 30 mg/mL to about 60 mg/mL.

The pharmaceutical formulation disclosed herein having solution stability over more than 24 hours, compared to JEVTANA®, which rapidly loses cabazitaxel content within only 4 hours.

In some embodiments, the pharmaceutical formulation for ready-to-use can include an albumin component in addition to the components of ready-to-dilute formulation: solvents, solubilizer and surfactant. This formulation is stable in aqueous media for 30 days with no drug precipitation. The albumin component can be an aqueous solution of albumin at a concentration of at least 10%, 15%, 20%, 25%, 30% or 35% (w/w), and can be present in the final ready-to-use formulation in an amount of at least 75%, 80%, 85%, 90% or 95% (w/w) relative to the other components in the formulation.

In certain embodiments, the pharmaceutical formulations include cabazitaxel in free form or in bound form with albumin.

In embodiments, the pharmaceutical formulations of the application comprise aqueous or non-aqueous solvent systems, or suitable mixtures thereof.

The persons skilled in the art will understand that when the solvent system is described as non-aqueous, this merely indicates that water is not a substantial component of the formulation. There may be some water present in the formulation due to its presence in some of the commercial components used (e.g., surfactants), and water may also be absorbed from the environment into the formulation.

Cabazitaxel is practically insoluble in water but has good solubility in alcohols. However, alcohols alone are not useful for cabazitaxel administration, because a large amount of alcohol associated with high dose requirement of cabazitaxel may result anaphylactic or alcoholism manifestations, resulting in serious adverse events. Pharmaceutically acceptable solubilizers should be also added into the formulation in addition to alcohols.

In some embodiments, the pharmaceutically acceptable non-aqueous solvent system may include any pharmaceutically acceptable non-aqueous solvent in which the cabazitaxel is soluble, for example, ketones such as acetone, and alcohols such as ethanol, benzyl alcohol, tertiary-butyl alcohol, isopropyl alcohol, and mixtures thereof. In some embodiments, the solvent can be present in an amount of about 0.1% to about 10.0% of the total weight of the formulation.

Ethanol is can be used as a solvent, as it has anti-microbial and antifoaming properties. Other solvents include diethylene glycol monoethyl ether, DMA, DMSO, propylene glycol and glycofurol.

The formulation can include one or more pharmaceutically acceptable surfactants. Suitable surfactants include anionic, cationic, amphoteric and non-ionic surfactants, Exemplary non-ionic surfactants include polyethylene oxides, for instance PEG 300 or PEG 400. Pharmaceutically acceptable surfactant for this application include, but are not limited to, polysorbate or polyethoxylated castor oil, Polyoxyl 20 stearate, Polyoxyl 35 castor oil, poloxamer, polyoxyethylene sorbitan monoisostearate, polyethylene glycol 40 sorbitan diisostearate, Polyoxyl 40 Hydrogenated castor oil, Polysorbate, Polysorbate 20, Polysorbate 40, Polyoxyl 60 stearate, Polysorbate 85, Polysorbate 60, poloxamer 331, polyoxyethylene fatty acid esters, Polyoxyl 40 castor oil, poloxamer 188, polyoxyethylene polyoxypropylene 1800, oleic acid, Sodium desoxycholate, Sodium lauryl sulfate, Sorbitan monolaurate, Sorbitan monooleate, Sorbitan monopalmitate, Sorbitan trioleate, N-Carbamoyl methoxypolyethylene glycol 2000-1,2-distearol, myristic acid, Steareth, Stearic acid, Polyoxyl 40 stearate, Sucrose stearate, Tocopherol, polyoxyl castor oil, Triglyceride synthetic, Trimyristin, Tristearin, magnesium stearate, lecithin, lauryl sulfate, Vitamin E, egg yolk phosphatides, docusate sodium, Polysorbate 80, dimyristoyl phosphatidylglycerol, dimyristoyl lecithin, Capryol 90 (propylene glycol monocaprylate), Capryol PGMC (propylene glycol monocaprylate), deoxycholate, cholesterol, Cremophor EL, Propylene glycol alginate, Croval A-10 (PEG 60 almond glycerides), Labrafil 1944 (oleoyl macrogol-6 glycerides), Labrafil 2125 (linoleoyl macrogol-6 glycerides), Labrasol (caprylocaproyl macrogol-8 glycerides), Lauroglycol 90 (propylene glycol monolaurate), Lauroglycol FCC (propylene glycol laurate), calcium stearate, Lecithin Centromix E, Lecithin Centrophase 152, Lecithin Centrol 3F21B, POE 26 glycerin, Olepal isosteariques (PEG-6 isostearate), Plurol diisostearique (polyglycerol-3-diisostearate), Plurol Oleique CC, POE 20 Sorbitan trioleate, Tagat TO (polyoxyethylene glycerol trioleate), or Solutol (macrogol-15 hydroxystearate). In some embodiments, the surfactant can be present in an about 10% to about 90% of the total weight of the ready-to-dilute formulation, preferably from about 30% to about 60% of the total weight of the ready-to-dilute formulation, Pharmaceutically acceptable solubilizers for the present application may be defined as substances that maximize the solubility of a practically insoluble drug like cabazitaxel. Solubility enhancement with the incorporation of solubilizer may involve micellar solubilization, cosolvency, complexation, prodrug formation, or salt formation. Pharmaceutically acceptable solubilizer for this application include, but are not limited to, macrogol 15 hydroxysterate, PEG 400, TPGS, Ethanol, MCT, Glycofurol, DMSO, DMA, diethylene glycol monoethyl ether, caprylocaproyl polyoxylglycerides.

In some embodiments, the solubilizer is about 10 to about 90% of the total weight of the formulation, preferably is about 30% to about 60% the total weight of the formulation.

In some embodiments, the solubilizer can include one or more compounds having the formula:

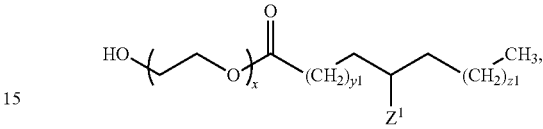

wherein x is an integer from 1-20, preferably 4-20, more preferably from 6-18, even more preferably from 6-14, and especially preferably from 8-12; y1 is an integer from 2-20, preferably from 4-16, more preferably from 6-14, and even more preferably from 8-12; z1 is an integer from 1-15, preferably from 2-12, more preferably from 2-10, and even more preferably from 3-8; and $Z^1$ is selected from hydrogen or the group OR, in which R is selected from hydrogen and a group having the formula:

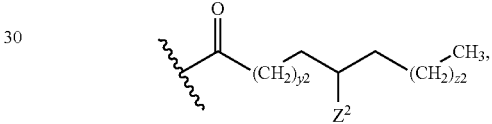

wherein y2 is an integer from 2-20, preferably from 4-16, more preferably from 6-14, and even more preferably from 8-12; z2 is an integer from 1-15, preferably from 2-12, more preferably from 2-10, and even more preferably from 3-8; and $Z^2$ is selected from hydrogen or hydroxyl.

In some embodiments, the solubilizer is macrogol 15 hydroxystearate, which is also known as Solutol or Kolliphore HS or polyoxyl 15 hydroxystearate.

Macrogol 15 hydroxystearate consists of polyglycol mono- & di-esters of 12-hydroxystearic acid and wherein small part of 12-hydroxy group can be etherified with polyethylene glycol and represented by following structure

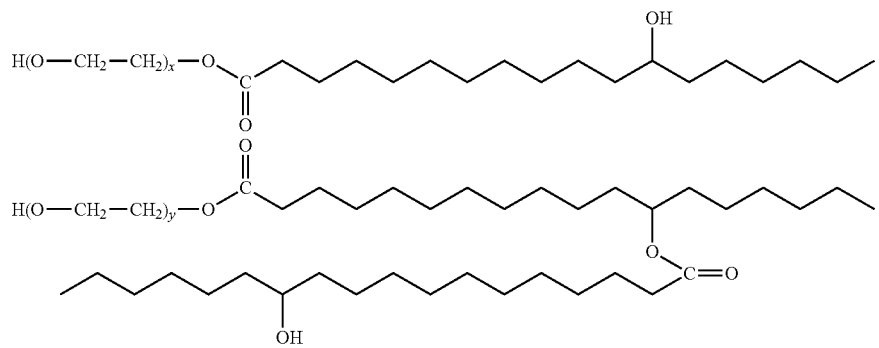

The applicant has surprisingly found that using macrogol 15 hydroxystearate in cabazitaxel formulation increases solution stability up to 24 hours. Polyethylene glycols (PEG) are polymers of ethylene oxide and usually designated by a numerical value, which is indicative of the average molecular weight for a given grade. Molecular weights below 600 typically are liquids, and molecular weights above 1000 typically are solids at room temperature. These polymers are readily soluble in water, which make them quite useful for parenteral products. These polymers are generally regarded as nontoxic and nonirritant In some embodiments, the pharmaceutical formulation includes one or more compounds of the formula:

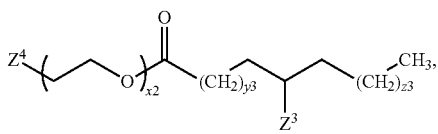

wherein x2 is an integer from 1-20, preferably 4-20, more preferably from 6-18, even more preferably from 6-14, and especially preferably from 8-12; wherein y3 is an integer from 1-20, preferably from 2-16, more preferably from 2-14, and even more preferably from 2-6; z3 is an integer from 0-15, preferably from 1-10, more preferably from 2-7, and even more preferably from 2-4; in certain embodiments, z3 is zero; $Z^3$ is selected from hydroxyl and hydrogen, and $Z^4$ is selected from hydroxyl or the group:

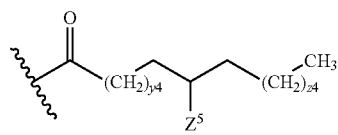

wherein y4 is an integer from 1-20, preferably from 2-16, more preferably from 2-14, and even more preferably from 2-6; z4 is an integer from 0-15, preferably from 1-10, more preferably from 2-7, and even more preferably from 2-4; $Z^5$ is selected from hydrogen or hydroxyl. In certain embodiments, z4 is zero.

In some instance, the formulation include one or more caprylocaproyl polyoxylglycerides which are also known as caprylocaproyl macrogolglycerides, Polyoxyl glyceryl caprylocaprate, PEG-8 caprylic/capric glycerides, Labrasol®, Labrasol® ALF is an oil-in-water surfactant used to solubilize active pharmaceutical ingredients and promote drug penetration and permeation. & it is mixture of caprylocaproyl macrogolglycerides, which are also known as PEG-8 caprylocaproyl glycerides, and are obtained by performing polyglycolysis of medium chain triglycerides with PEG-8 (molecular mass=400) represented by following structures

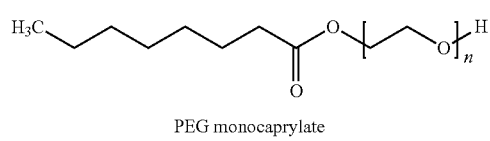

PEG monocaprylate

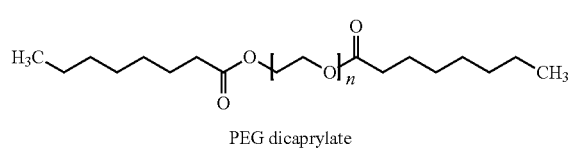

PEG dicaprylate

In certain embodiments, the pharmaceutical formulations of application comprises diethylene glycol monoethyl ether which is also known as Ethoxydiglycol, Carbitol, Ethyl Carbitol, Transcutol, Transcutol HP, Transcutol P is commonly use as solvent and has the formula $CH_3CH_2OCH_2CH_2OCH_2CH_2OH$.

A person skilled in the art of preparing formulations according to the present invention will understand that the proportions of components with respect to each other will vary depending on the specific components used. For example, the use of different surfactants and alcohols will require some straightforward modifications to the proportions, depending on the miscibility of a particular surfactant in a particular alcohol.

In some embodiments, the excipients may be selected for the present invention may be selected from but not limited to the range of pharmaceutically acceptable excipients, which are soluble in the non-aqueous solvent system and which are compatible with the active ingredient. The excipients selected for the purpose of the present invention should not create any degenerative effect on the active ingredient such as cabazitaxel. In some instances the scope of application present invention also covers incorporation of pharmaceutically acceptable excipients useful to counteract the degenerative effect of any of the other excipients present in the formulation.

A person skilled in the art will be aware that pH is a measure of free hydrogen ions in a solution. For example, free hydrogen ions will exist in alcohol systems that contain acids. The pH may be measured by placing a pH meter electrode directly into liquid formulations, such pH meter having been calibrated for the appropriate pH range with standard aqueous buffers. Persons skilled in the art will know of other methods which may be used to measure pH. Such persons will further know that, while the pH meter reading obtained for a substantially non-aqueous formulation may not be a true reflection of the actual hydrogen ion concentration in the solution, it may nonetheless give a meaningful and reproducible measurement that indicates the relative acidity/basicity of the solution, as is the case for the cabazitaxel formulations disclosed herein. In instances, the pH meter reading will be in the range from about 3 to 9, or from about 3 to 6, or from about 4 to 6. These ranges are for measurements made at room temperature (20-25° C.). A person skilled in the art will know that the pH meter reading will vary somewhat, depending on the temperature.

The acids may be any pharmaceutically acceptable acids known to those skilled in the art, which are soluble in a non-aqueous solvent system and are compatible with cabazitaxel. A person skilled in the art will know that certain strong acids may react with cabazitaxel, creating degradants, and to avoid such acids. For example, epimerization of the hydroxyl functionality of cabazitaxel is known to be facilitated by certain strong acids. In some instances, the use of a stabilizing agent may counteract any degradation effect of the acid. The acids may be inorganic or organic. In certain embodiments, a pharmaceutically acceptable acid includes a monocarboxylic, dicarboxylic or tricarboxylic acid. Useful examples include, but are not limited to, citric acid, tartaric acid, acetic acid, and any mixtures thereof, preferably citric acid is used. The acid can be present in an amount about 0.1% to about 1.0% of the total weight of the formulation.

A person skilled in the art will know that the amount of pharmaceutically acceptable acid used will be limited by the particular acid's solubility in the pharmaceutically acceptable non-aqueous solvent system. The amount of acid required will also be further determined by the relative strength of the acid. When the pharmaceutically acceptable acid is citric acid, in embodiments the citric acid is present at concentrations in the range of from about 1 to 8 mg/mL.

The albumin can function as both a solubilizer and stabilizer. We have found that cabazitaxel albumin formulations are stable for 30 days, compared to reference product which is loses cabazitaxel content after only four hours. The cabazitaxel/albumin formulations will include a suitable solvent, for instance an alcohol (ethanol), sterile water for injection, polysorbate 80, PEG 300, PEG 400, propylene glycol and suitable mixtures thereof. A person skilled in the art preparing formulations according the application will understand that the proportions of components with respect to each other in diluent formulation will vary depending on the specific components used and solubility of cabazitaxel.

The addition of the components of the single-vial and dual-vial injection concentrates can be achieved by methods known in the art. For example, one or more of the components may be added to each other and then into a common receptacle for mixing, or the components may be added to a common receptacle in a particular order, or the components may be added to a common receptacle simultaneously. In certain embodiments, the cabazitaxel, or other lipophilic molecule, and the solubilizer are combined separately from the other components. In some embodiments, the cabazitaxel, or other lipophilic molecule is dissolved in the solubilizer separately from the other components.

The components of the single-vial and dual-vial injection concentrates may be mixed by methods known in the art. For example, the components can be mixed by simple mixing, or may be mixed with a mixing device continuously, periodically, or a combination thereof. Mixing devices may include, but are not limited to, a magnetic stirrer, shaker, a paddle mixer, homogenizer, and any combination thereof.

The addition and mixing of one or more components of the single-vial and dual-vial injection concentrates may occur under controlled conditions. For example, the addition and mixing of the components may occur under conditions such as under nitrogen or at a particular humidity, etc., or the adding and mixing may occur under certain temperatures. In certain embodiments, the adding and mixing may occur under temperature conditions of about 25° C. to about 80° C.

Additionally, the addition and mixing may be under controlled light exposure, such as in yellow light or under protection from direct exposure to light. After the injection concentrate is prepared, it may be sterilized by methods known in the art. The injection concentrate may undergo aseptic filtration (e.g., using a 0.2 µm disposable pre-sterilized membrane filter). Additionally, the injection concentrate may be placed into a container (e.g., an intravenous solution bag, bottle, vial, ampoule, or pre-filled sterile syringe). The container may have a sterile access port for piercing by a hypodermic injection needle. In some embodiments, the injection concentrate may be filled in one or more pre-sterilized depyrogeneated vials and stopped aseptically with a pre-sterilized butyl stopper.

The diluted injection concentrate may be formed by mixing the dual-vial injection concentrate and diluent together. In one embodiment the dual-vial injection concentrate may be added to the diluent. In another embodiment, the diluent may be added to the dual-vial injection concentrate. In yet another embodiment, the dual-vial injection concentrate and diluent may be combined together in a pre-sterilized vessel. The dual-vial injection concentrate and diluent may be mixed by repeated inversions, swirling, or other techniques known in the art. Due the absence of polysorbates in the diluent and the dual-vial injection concentrate, little to no foaming occurs during the mixing.

The final dilution for infusion may be prepared by combining a single-vial injection concentrate or a diluted injection concentrate with an infusion solution of the present invention, according to methods known in the art. For example, the single-vial injection concentrate or a diluted injection concentrate may be mixed with an infusion solution in a common receptacle, or the single-vial injection concentrate or the diluted injection concentrate may be injected into an infusion bag containing the infusion solution.

An embodiment of present invention is directed to delivery of cabazitaxel, once diluted to appropriate injection (especially infusion, most particularly IV infusion) concentrations, it may be administered in appropriate amounts for treating cabazitaxel responsive conditions known in the art.

An embodiment of the present invention, there is provided a method for treating patients with hormone-refractory metastatic prostate cancer previously treated with a docetaxel-containing treatment regimen in combination with prednisone by administering stable ready-to-use parenteral formulation of cabazitaxel. In some instances, a stable ready-to-dilute formulation is combined with an appropriate solvent and administered parenterally to a patient in need thereof.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

Cabazitaxel Formulation Injection Formulation

The following formulation classes, each containing 1-5% cabazitaxel and 0.1-1.5% citric acid can be prepared with the following solubilizers, surfactants, and solvents (MHS=macrogol-15-hydroxystearate; MCT=medium chain triglycerides)

| # | Sol. (5-50%) | Surf. (5-45%) | Solvent (0-50%) |
|---|---|---|---|
| A | MHS | PEG 400 | Ethanol |
| B | MHS | PEG 400 | Transcutol |
| C | MHS | PEG 400 | DMA |
| D | MHS | PEG 400 | DMSO |

-continued

| # | Sol. (5-50%) | Surf. (5-45%) | Solvent (0-50%) |
|---|---|---|---|
| E | MHS | PEG 400 | DMSO |
| F | MHS | PEG 400 | — |
| G | MHS | PEG 400 | Propylene glycol |
| H | MHS | PEG 400 | t-BuOH |
| I | Lecithin | Polaxomer 188 | Ethanol |
| J | MHS | MCT | Labrasol |
| K | Lecithin | Polaxomer 188 | Ethanol + Cremophor EL (0-10%) |
| L | MHS | PEG 400 | Propylene glycol |

Citric acid was dissolved in the solvent under stirring at room temperature, followed by addition of cabazitaxel. Surfactant was added and stirred at 60° C. until a clear solution was observed. The solubilizer was then added and stirred until dissolved; the resulting solution was aseptically filtered and sealed in a suitable container.

Example 2

Cabazitaxel Formulation Injection Using Albumin

The following formulations, each containing 1-5% cabazitaxel and 0.1-1.5% citric acid can be prepared Table 2 (Examples A-G)

| # | Sol. (5-50%) | Surf. (0-45%) | Solvent (0-50%) |
|---|---|---|---|
| A | MHS | PEG 400 | Ethanol |
| B | MHS | PEG 400 | Transcutol |
| C | MHS | PEG 400 | DMSO |
| D | MHS | PEG 400 | DMA |
| E | MHS | PEG 400 | Glycofurol |
| F | MHS | PEG 400 | — |
| G | Kolliphor HS 15 | | Ethanol |

Citric acid was dissolved in the solvent under stirring at room temperature, followed by addition of cabazitaxel. Surfactant was added and stirred at 60° C. until a clear solution was observed. The solubilizer was then added and stirred until dissolved. The resulting solution was diluted with 25% albumin solution in a 5:95 ratio, the resulting solution is aseptically filtered and sealed in a suitable container.

Example 3

Cabazitaxel Ready to Dilute Composition

| Ingredients | Qty (mg/2 ml) |
|---|---|
| Cabazitaxel | 60.00 |
| Citric acid anhydrous | 10.00 |
| Ethanol | 100.00 |
| Polyethylene glycol 400 | 900.0 |
| Macrogol 15 hydroxystearate | 1000 |

Example 4

Cabazitaxel Ready to Dilute Composition

| Ingredients | Qty (mg/2 ml) |
|---|---|
| Cabazitaxel | 60.00 |
| Lactic acid crystals | 200.00 |
| Labrasol | 900.00 |
| Transcutol HP | 1000.0 |

Example 5

Cabazitaxel Ready to Use Composition

| Ingredients | Qty (mg/2 ml) |
|---|---|
| Cabazitaxel | 60.00 |
| Citric acid anhydrous | 10.00 |
| Ethanol | 100.00 |
| Polyethylene glycol 400 | 900.0 |
| Macrogol 15 hydroxy-sterate | 1000 |
| Human serum albumin | q.s. 250 mL |

Stability Study

Example 3 was diluted with 5% dextrose solution formulation as well as commercial formulation were studies for stability of solution with respect to assay values using HPLC method. The results are shown in table 3.

TABLE 3

| Commercial Formulation | | RTD formulation diluted with 5% Dextrose solution | | | |
|---|---|---|---|---|---|
| 0 Hr | 24 Hr | 0 Hr | 4 Hr | 8 Hr | 24 Hr |
| 104.00% | 27.90% | 101.30% | 102.10% | 105.20% | 87.90% |

Similarly ready to use formulation comprising albumin solution as well as commercial formulation were studies for stability of solution with respect to assay values. The results are shown in table 4.

TABLE 4

| Commercial Formulation | | Example 5 | | | |
|---|---|---|---|---|---|
| | | | 1 Month | 1 Month | 1 Month |
| 0 Hr | 24 Hr | Initial | 2-8° C. | 30° C. | 40° C. |
| 104.00% | 27.90% | 109.30% | 109.40% | 103.20% | 104.90% |

The composition of Example 3 as well as Example 5 were subjected accelerated stability testing. The results of stability of Example 3 are shown in table 5 and the results of stability of Example 5 are shown in table 6.

TABLE 5

|  | t = 0 | 1 month | | | | 3 month | | | | 6 month | | | | 12 month | |
| --- | --- | --- | --- | --- | --- | --- | --- | --- | --- | --- | --- | --- | --- | --- | --- |
| Conditions | | A | B | C | D | A | B | C | D | A | B | C | D | A | B |
| Assay | 101.4 | ND | ND | ND | ND | 107.2 | 107 | 106.9 | 107.4 | 104.4 | 100.3 | 101.4 | 99.6 | 102.6 | 105.3 |
| Related Substance | 0.12 | ND | ND | ND | ND | 0.25 | 0.11 | 0.11 | 0.55 | <0.1 | <0.1 | <0.1 | <0.1 | <0.1 | <0.1 |
| Assay | 105.6 | ND | ND | ND | ND | 108.2 | 106.6 | 105.0 | 107.1 | 102.2 | 102.8 | 102.9 | 101.2 | 103.9 | 103.6 |
| Related Substance | 0.23 | ND | ND | ND | ND | 0.11 | 0.23 | 0.11 | 0.13 | <0.1 | <0.1 | <0.1 | 0.70 | <0.1 | <0.1 |
| Assay | 105.5 | ND | ND | ND | ND | 105.8 | 106.4 | 107.2 | 106.7 | 104.4 | 103.6 | 103.3 | 103.0 | 102.8 | 102.7 |
| Related Substance | 0.21 | ND | ND | ND | ND | 0.10 | ND | 0.10 | 0.14 | <0.1 | <0.1 | <0.1 | 0.37 | 0.18 | <0.1 |

TABLE 6

|  | t = 0 | 1 month | | | | 3 month | | | | 6 month | | | | 12 month | |
| --- | --- | --- | --- | --- | --- | --- | --- | --- | --- | --- | --- | --- | --- | --- | --- |
| Conditions | | A | B | C | D | A | B | C | D | A | B | C | D | A | B |
| Assay | 105.6 | ND | ND | ND | ND | 108.2 | 106.6 | 105.0 | 107.1 | 102.2 | 102.8 | 102.9 | 101.2 | 103.9 | 103.6 |
| Related Substance | 0.23 | ND | ND | ND | ND | 0.11 | 0.23 | 0.11 | 0.13 | <0.1 | <0.1 | <0.1 | 0.70 | <0.1 | <0.1 |
| Assay | 101.4 | 108 | 108.2 | 107.1 | 108.3 | ND | ND | 99.0 | ND | 103.0 | 102.8 | 105.6 | 105.4 | 101.1 | 104.2 |
| Related Substance | 0.10 | 0.08 | 0.08 | 0.08 | 0.09 | ND | ND | 0.23 | ND | <0.1 | <0.1 | <0.1 | <0.1 | <0.1 | <0.1 |
| Assay | 102.6 | 109.8 | 110.5 | 109.8 | 109.8 | ND | ND | ND | ND | 105.7 | 105.7 | 98.3 | 98.6 | 102.8 | 104.1 |
| Related Substance | 0.23 | 0.09 | 0.03 | 0.13 | 0.10 | ND | ND | ND | ND | <0.1 | <0.1 | 0.65 | 0.52 | <0.1 | <0.1 |
| Assay | 102.1 | 103 | 108.2 | 107.6 | 107.7 | 95.4 | 103.6 | 98.9 | 100.7 | 103.1 | 103.0 | 98.5 | 97.9 | 106.6 | 106.3 |
| Related Substance | 0.22 | 0.08 | 32.47 | 0.07 | 0.10 | <0.1 | <0.1 | 0.11 | 0.13 | <0.1 | <0.1 | 0.36 | 0.36 | <0.1 | <0.1 |

Key-A = 2-8° C.; B = 25° C./60% RH; C = 30° C./75% RH; D = 40° C./75% RH

The following in vivo assays compare the pharmacokinetic and efficacy of formulations prepared according to the instant invention with commercially available JEVTANA®.

Single Dose Comparative Intravenous Infusion (1 Hour) Pharmacokinetic Study of Cabazitaxel in Rats Method and Material

| Test System | Wistar Rat |
| --- | --- |
| Sex | Male |
| Rationale | Wistar Rats are used as it is commonly used rodent species in the pharmacokinetic evaluation of drugs, and acceptable to the regulatory authorities. |
| Source of animals | Animal Research Facility, Suven Life Sciences Ltd. |
| Total no of animals | 20 |
| Age at study/ Body Weight | 8 to 12 weeks/250-270 g (±20% variation accepted at the time of dosing) |
| Veterinary Examination | Prior to the final assignment to the study, rats will be subjected to veterinary examination to ensure that the selected rats are in a good state of health |
| Animal Identification | Animals will be uniquely identified by tail marking with permanent marker. |
| Acclimatization | On receipt from supplier, the animals will be examined for external signs of ill health prior to acceptance. After health examination, animals will be acclimatized for one week under test conditions. Only animals without any visible signs of illness will be used for the study |
| Grouping and Randomization | The animals for the experiment will be weighed and arranged in ascending order of their body weights. |
| Test System | Wistar Rat |
| | These stratified body weight of rat will be distributed by randomization procedure using Microsoft excel spreadsheet to all the experimental groups, such that body weight variation of animals selected for the study does not exceed ±20% of the mean body weight. |
| Animal catheterization | Under isoflurane anesthesia, all animals will be cannulated in right external jugular vein and femoral vein (for intravenous infusion, PE-10 tubing). Rats will be surgically implanted with a catheter (external jugular vein, PE-50 tubing) for repeated withdrawal of blood samples (~0.300 mL volume per predetermined blood collection time). Each group one standby animals will be catheterized as backup. Rats will be allowed to recover for minimum of 48 h after cannulation before inclusion in study and drug administration. General animal health and cannula patency will be confirmed prior to dose administration. |

Test Item: JEVTANA® (Injection/& 40 mg/mL) and Test Cabazitaxel Formulation.

JEVTANA® requires two dilutions prior to administration as provided below:

Step 1: Initial dilution of the concentrate for solution for infusion with the supplied solvent.

Step 1.1: Inspect the concentrate vial and the supplied solvent. The concentrate solution should be clear.

Step 1.2: Using a syringe fitted with a needle, aseptically withdraw the entire contents of the supplied solvent by partially inverting the vial.

Step 1.3: Inject the entire contents into the corresponding concentrate vial. To limit foaming as much as possible when injecting the solvent, direct the needle onto the inside wall of the vial of concentrate solution and inject slowly. Once reconstituted, the resultant solution contains 10 mg/mL of cabazitaxel.

Step 1.4: Remove the syringe and needle and mix manually and gently by repeated inversions until obtaining a clear and homogeneous solution. It could take approximately 45 seconds.

Step 1.5: Let this solution stand for approximately 5 minutes and check then that the solution is homogeneous and clear. It is normal for foam to persist after this time period. This resulting concentrate solvent mixture contains 10 mg/mL of cabazitaxel (at least 6 ml deliverable volume). The second dilution should be done immediately (within 1 hour) as detailed in Step 2. More than one vial of the concentrate solvent mixture may be necessary to administer the prescribed dose.

Step 2: Second (final) dilution for infusion

Step 2.1: Aseptically withdraw the required amount of concentrate solvent mixture (10 mg/mL of cabazitaxel), with a graduated syringe fitted with a needle. As an example, a dose of 45 mg JEVTANA would require 4.5 mL of the concentrate solvent mixture prepared following Step 1. Since foam may persist on the wall of the vial of this solution, following its preparation described in Step 1, it is preferable to place the needle of the syringe in the middle when extracting.

Step 2.2: Inject in a sterile PVC free container of 5% glucose solution for infusion. The concentration of the infusion solution will be 0.20 mg/mL. Mix the content of the infusion bottle manually using a rocking motion. This solution will be filled in to PVC free syringe and 2.5 mg/kg dose equivalent volume (E.g. 3.125 mL of 0.2 mg/mL solution/ 250 gram rat, rate of infusion 12 mL/kg/hr) will be infused to each animal. Note: Do not use PVC infusion containers or polyurethane infusion sets for the preparation and administration of JEVTANA. After final dilution in the infusion bottle:

Test Formulation Cabazitaxel Formulation Requires Following Dilutions Prior to Administration Step 1: Initial Test Formulation Cabazitaxel Formulation will contain the 30 mg/mL solution.

Step 1.1: Aseptically withdraw the 0.500 mL amount of 30 mg/mL of cabazitaxel formulation solution in to a clean bottle, with a graduated syringe fitted with a needle.

Step 1.2: To that add 75 mL of 5% glucose solution, the concentration of the final infusion solution will be 0.20 mg/mL. Mix the content of the infusion bottle manually using a rocking motion. This solution will be filled in to PVC free syringe and 2.5 mg/kg dose equivalent volume (3.125 mL of 0.2 mg/mL solution/250 gram rat, rate of infusion 12 mL/kg/hr.) will be infused to each animal.

Formulation analysis and short term stability: Stability of the infusion solution will be demonstrated for 4 hours at ambient temperature (including the 1 hour infusion time) before initiation of the in-life portion Route of administration: Intravenous slow infusion for one hour.

Intravenous Infusion: Infusion system includes a swivel (Instech, USA), tubing (Co-ex infusion tubing), syringes and an infusion pump (Pico plus -Harvard apparatus). Swivel, a device that rotates to keep the tubing from tangling, is a critical part of animal infusion system. Glass syringes (Hamilton) are fixed on to the infusion pumps, Tubing is used in connecting the glass syringes to swivel at one end and swivel to animal at other end. Each rat was administered at a 2.5 mg/kg single dose of JEVTANA or Cabazitaxel RTU by IV infusion for 1 h with an Infusion volume of 12 mL/kg/ hr.

| Group | | Animal ID No. | Dose | Formulation strength (mg/mL) |
|---|---|---|---|---|
| G1 | Jevtana ® | 1-10 | 2.5 mg/kg | 0.20 |
| G2 | Test Formulation | 11-20 | 2.5 mg/kg | 0.20 |

Blood Collection and Storage of Samples

| | |
|---|---|
| Site of blood collection | External Jugular vein |
| Volume of blood collected | 0.30 mL (approx.) at each time point |
| Anticoagulant | Sodium heparin (Stock: 1000 IU/mL; 10 μL/0.30 mL blood) |
| Blood collection time points | 0 (pre-dose), 0.5, 1, 1.25, 1.50, 2, 4, 6, 8, 10, 24 hr post-dose; Total 11 bleedings/rat |
| Blood centrifugation | 5000 rpm for 5 minutes at 4° C. |
| Plasma storage | −70° C. until analysis (two aliquots of ~0.1 mL each) |
| Plasma vials labelling details | Study No., animals ID No., time point, group, aliquot no. etc. |

Note:
A pre-dose sample (three animals from each group) will be collected at pre-dose within 1.0 hour prior to dose administration. Blood samples will be kept on ice bath till centrifugation and centrifugation should be done within 30 minutes of collection.

On completion of last blood sampling, animals will be sacrificed and carcasses discarded.

Bioanalysis: Plasma samples from group will be analyzed for Cabazitaxel concentrations Bioanalysis will be performed by fit-for-purpose analytical method using LC-MS/MS.

Pharmacokinetic data analysis and Evaluation: Phoenix® Software, version 6.4, USA was used for studying Pharmacokinetic parameters such as $C_{max}$, $T_{max}$, Kel, $T_{1/2}$, AUC (0-t), AUC (0-∞), VD, Geometric means, 90 percent Confidence intervals (CI). Bioequivalence will be calculated for Reference (JEVTANA®) vs test formulation.

Results

| Cabazitaxel Plasma Concentrations (ng/mL) | | |
|---|---|---|
| Time | JEVTANA | Test formulation |
| 0 Hr | 0 | 0 |
| 0.5 Hr | 190.4 | 256.2 |
| 1 Hr | 166.8 | 177.6 |
| 1.25 Hr | 57.2 | 52.9 |
| 1.5 Hr | 43.0 | 36.7 |
| 2 Hr | 32.9 | 23.1 |
| 4 Hr | 13.4 | 10.9 |
| 6 Hr | 8.0 | 6.5 |
| 8 Hr | 5.6 | 5.8 |
| 10 Hr | 4.7 | 4.8 |
| 24 Hr | 2.2 | 2.1 |

Study 2: Comparative Pharmacokinetics

Method and Material

| Test System | Wistar Rat |
|---|---|
| Sex | Male |
| Rationale | Wistar Rats are used as it is commonly used rodent species in the pharmacokinetic evaluation of drugs, and acceptable to the regulatory authorities. |
| Source of animals | Animal Research Facility, Suven Life Sciences Ltd. |
| Total no of animals | 16 |
| Age at study/ Body Weight | 8 to 12 weeks/250-270 g (±20% variation accepted at the time of dosing) |
| Veterinary Examination | Prior to the final assignment to the study, rats will be subjected to veterinary examination to ensure that the selected rats are in a good state of health |
| Animal Identification | Animals will be uniquely identified by tail marking with permanent marker. |
| Acclimatization | Animals were acclimatize as per standard protocol |
| Grouping and Randomization | Animals were grouped & randomized as per standard protocol |
| Animal catheterization | Animal were catheterized using standard protocol |
| Feed and Water | Animals were provided feed and water as per standard protocol This study will be conducted in overnight fasted (~8 hrs) male Wistar rats. Post dose animals will be fasted for another 2 hours. Animals will be deprived of water for about 1 hour, pre- and post-dosing. |
| Animal handling | Experiment will be carried out by qualified & trained scientific personnel's (trained in animal handling, drug administration and experimentation). |

Test Item: Jevtana® (Injection/& 40 mg/mL) and Test Cabazitaxel Formulation.

JEVTANA® requires two dilutions prior to administration as provided in package insert of JEVTANA®

As per JEVTANA® literature, chemical and physical stability of the infusion solution has been demonstrated for 8 hours at ambient temperature (including the 1 hour infusion time) and for 48 hours at refrigerated conditions (including the 1 hour infusion time) as per label. Stability testing is not required.

Test Formulation Cabazitaxel Formulation Requires Following Dilutions Prior to Administration Step 1: Initial Test Formulation Cabazitaxel Formulation will contain the 30 mg/mL solution.

Step 1.1: Aseptically withdraw the 0.8 mL amount of 30 mg/mL of cabazitaxel formulation solution in to a clean bottle, with a graduated syringe fitted with a needle.

Step 1.2: To that add 99.2 mL of 5% glucose solution, the concentration of the final infusion solution will be 0.24 mg/mL. Mix the content of the infusion bottle manually using a rocking motion. This solution will be filled in to PVC free syringe and 1.25 mg/kg dose equivalent volume at 5.21 mL/kg will be infused to each animal.

Formulation analysis and short term stability: Stability of the infusion solution will be demonstrated for 4 hours at ambient temperature (including the 1 hour infusion time) before initiation of the in-life portion Route of administration: Intravenous slow infusion for one hour.

Intravenous Infusion: Infusion system includes a swivel (Instech, USA), tubing (Co-ex infusion tubing), syringes and an infusion pump (Pico plus -Harvard apparatus). Each rat was administered at a 1.25 mg/kg single dose of Cabazitaxel (JEVTANA®) or Cabazitaxel RTU (Cipla) by IV infusion for 1 h with an Infusion volume of 5.21 mL/kg.

| Group | | Animal Number per group | Dose | Formulation strength (mg/mL) |
|---|---|---|---|---|
| G1 | JEVTANA ® | 8 | 1.25 mg/kg | 0.24 |
| G2 | Test Formulation | 8 | 1.25 mg/kg | 0.24 |

Blood collection and storage of samples: The Blood was collected from External Jugular Vein at approximate volume of 0.30 mL using Sodium heparin (Stock: 1000 IU/mL; 10 µL/0.30 mL blood) at each of following time point; 0 (pre-dose), 0.5, 1, 1.25, 1.50, 2, 4, 6, 8, 10, 24hr post-dose. The blood was further processed as per standard protocol to separate plasma. The plasma vials were labelled with following details; Study No., animals ID No., time point, group, aliquot no. etc.

Note: A pre-dose sample (three animals from each group) will be collected at pre-dose within 1.0 hour prior to dose administration. Blood samples will be kept on ice bath till centrifugation and centrifugation should be done within 30 minutes of collection.

On completion of last blood sampling, animals will be sacrificed and carcasses discarded.

Bioanalysis: Plasma samples from group will be analyzed for Cabazitaxel concentrations Bioanalysis will be performed by fit-for-purpose analytical method using LC-MS/MS with the acetonitrile protein precipitation technique, quantified in the calibration range of 1-2000 ng/mL or ng/g.

Pharmacokinetic data analysis and Evaluation: Phoenix® Software, version 6.4, USA was used for studying Pharmacokinetic parameters such as Cmax, Tmax, Kel, T½, AUC (0-t), AUC (0-∞), VD, Geometric means, 90 percent Confidence intervals (CI). Bioequivalence will be calculated for Reference (JEVTANA®) Vs Cipla formulation using linear trapezoidal with linear interpolation method. For all biological matrixes the pharmacokinetic parameters were calculated. The data was analysed and interpreted both biologically and statistically. T-test was applied for the group comparison.

TABLE 1

Plasma concentration (Mean ± SD; in ng/mL) of Cabazitaxel after intravenous (1 hour infusion) administration at 1.25 mg/kg dose in male Wistar rats

| PK time point (hour) | JEVTANA ® (Dose: 1.25 mg/kg, IV | Test Formulation (Dose: 1.25 mg/kg, IV |
|---|---|---|
| 0.5 | 126 ± 136 | 90.7 ± 21.7 |
| 1 | 95.3 ± 94.6 | 111 ± 103 |
| 1.25 | 22.1 ± 5.52 | 19.8 ± 3.28 |
| 1.5 | 15.3 ± 9.08 | 15.1 ± 3.91 |
| 2 | 12.4 ± 11.6 | 9.88 ± 3.16 |
| 4 | 4.79 ± 3.6 | 5.14 ± 1.32 |
| 6 | 3.55 ± 1.36 | 5.15 ± 1.78 |
| 8 | 2.42 ± 1.14 | 3.79 ± 1.53 |
| 10 | 1.7 ± 0.876 | 2.31 ± 0.519 |
| 24 | 1.41 ± 0.781 | 0.331 ± 0.567 |

Results

TABLE 2

Plasma pharmacokinetic parameters of Cabazitaxel after intravenous (1 hour infusion) administration at 1.25 mg/kg dose in male Wistar rats (all values in mean ± SD)

| PK parameter | | JEVTANA ®<br>(Dose: 1.25 mg/kg, IV) | Test Formulation<br>(Dose: 1.25 mg/kg, IV) |
|---|---|---|---|
| $C_{max}$ | (ng/mL) | 149 ± 148 | 90 ± 17 |
| $T_{max}$ | (hr)<br>(Median range) | 0.75 (0.50-2.0) | 0.50 (0.50-1.0) |
| $K_{el}$ | (1/hr) | 0.0874 ± 0.0777 | 0.167 ± 0.0896 |
| $t_{1/2}$ | (hr) | 15.5 ± 13.4 | 5.05 ± 2.04 |
| $AUC_{last}$ | (hr*ng/mL) | 170 ± 86 | 147 ± 55 |
| $AUC_{INF\_obs}$ | (hr*ng/mL) | 206 ± 82 | 162 ± 52 |

Conclusion: The pharmacokinetics studies shows that novel ready to dilute formulation of cabazitaxel is comparative & similar with respect to commercially available formulation JEVTANA®

Study 3

Method and Material

| Test System | Wistar Rat |
|---|---|
| Sex | Male |
| Rationale | Wistar Rats are used as it is commonly used rodent species in the pharmacokinetic evaluation of drugs, and acceptable to the regulatory authorities. |
| Source of animals | Animal Research Facility, Suven Life Sciences Ltd. |
| Total no of animals | 48 |
| Age at study/<br>Body Weight | 8 to 12 weeks/255-2840 g (±20% variation accepted at the time of dosing) |
| Veterinary<br>Examination | Prior to the final assignment to the study, rats will be subjected to veterinary examination to ensure that the selected rats are in a good state of health |
| Animal<br>Identification | Animals will be uniquely identified by tail marking with permanent marker. |
| Acclimatization | Animals were acclimatize as per standard protocol |
| Grouping and<br>Randomization | Animals were grouped & randomized as per standard protocol |
| Animal<br>catheterization | Animal were catheterized using standard protocol |
| Feed and Water | Animals were provided feed and water as per standard protocol. This study will be conducted in overnight fasted (~8 hrs) male Wistar rats. Post dose animals will be fasted for another 2 hours. Animals will be deprived of water for about 1 hour, pre- and post-dosing. |
| Animal handling | Experiment will be carried out by qualified & trained scientific personnel's (trained in animal handling, drug administration and experimentation). |

Test Item: Jevtana® (Injection/& 40 mg/mL) and Test Cabazitaxel Formulation

JEVTANA® solution as well as Test Formulation were prepared using method as covered under study 1.

Route of administration: Intravenous slow infusion for one hour.

Intravenous Infusion: Infusion system includes a swivel (Instech, USA), tubing (Co-ex infusion tubing), syringes and an infusion pump (Pico plus -Harvard apparatus). Each rat was administered at a 1.25 mg/kg single dose of Cabazitaxel (JEVTANA®) or Cabazitaxel RTD (Cipla) by IV infusion for 1 h with an Infusion volume of 5.21 mL/kg. Formulation strength required for infusion is 0.24 mg/mL.

| Group | | Animal<br>ID No. | Dose | Formulation<br>strength (mg/mL) |
|---|---|---|---|---|
| G1 | (JEVTANA ®) | 1-24 | 1.25 mg/kg | 0.24 |
| G2 | Test Formulation | 24-48 | 1.25 mg/kg | 0.24 |

Blood collection and storage of samples: The Blood was collected from Retro Orbital Plexus Puncture at approximate volume of 0.30 mL using Sodium heparin (Stock: 1000 IU/mL; 10 µL/0.30 mL blood) at each of following time point; 1, 2, 4, 8, 24 and 48 hr post dose post-dose. The blood was further processed as per standard protocol to separate plasma. The plasma vials were labelled with following details; Study No., animals ID No., time point, group, aliquot no. etc Note: In said study, following single intravenous dose, each rat was anesthetized using isoflurane anesthesia and blood was collected Blood samples will be kept on ice bath till centrifugation and centrifugation should be done within 30 minutes of collection.

On completion of last blood sampling animals were sacrificed humanely by decapitation and different tissue specimens viz. brain, heart, kidney, liver, lungs & spleen were collected, processed and analysed for tissue and plasma concentration of Cabazitaxel Isolated tissue specimens of brain, kidney, spleen, heart, lungs and liver were rinsed with ice cold water to remove blood and blotted with tissue paper. Each tissue was weighed, transferred into a glass beaker and ice cold water was added (i.e. four volumes to the weight of tissue) and homogenized using tissue-tearor (rotor/stator type tissue homogenizer). All tissue samples were homogenized using ice cold ultrapure water type-I. Two aliquots of plasma and tissues homogenates were transferred into respective pre-labelled tubes and stored at −70° C. until analysis.

Bioanalysis: Plasma samples from group will be analyzed for Cabazitaxel concentrations Bioanalysis will be performed by fit-for-purpose analytical method using LC-MS/MS with the acetonitrile protein precipitation technique, quantified in the calibration range of 1-2000 ng/mL or ng/g.

Pharmacokinetic data analysis and Evaluation: Phoenix® Software, version 6.4, USA was used for studying Pharmacokinetic parameters such as Cmax, Tmax, Kel, T1/2, AUC (0-t), AUC (0-∞), VD, Geometric means, 90 percent Confidence intervals (CI). Bioequivalence will be calculated for Reference (JEVTANA®) Vs Cipla formulation using linear trapezoidal with linear interpolation method. For all biological matrixes the pharmacokinetic parameters were calculated. The data was analysed and interpreted both biologically and statistically. T-test was applied for the group comparison.

TABLE 6

Tissue distribution of Cabazitaxel after intravenous (1 hour infusion) administration at 1.25 mg/kg dose in male Wistar rats

| | $C_{max}$<br>(ng/mL | $AUC_{last}$<br>(hr*ng/mL | $AUC_{INF\_obs}$<br>(hr*ng/mL |

TABLE 6-continued

Tissue distribution of Cabazitaxel after intravenous (1 hour infusion) administration at 1.25 mg/kg dose in male Wistar rats

| Treatment | Tissue | or ng/g) | $T_{max}$ (hr) | $K_{el}$ (1/hr) | $t_{1/2}$ (hr) | or hr*ng/g) | or hr*ng/g) |
|---|---|---|---|---|---|---|---|
| JEVTANA ® | Brain | 12.4 | 1 | 0.333 | 2.08 | 62.6 | 67.2 |
| | Heart | 2410 | 1 | 0.0482 | 14.37 | 23700 | 25800 |
| | Kidney | 7850 | 1 | 0.0472 | 14.69 | 74100 | 81900 |
| | Liver | 1390 | 1 | 0.0487 | 14.23 | 6790 | 7270 |
| | Lungs | 5410 | 1 | 0.0412 | 16.83 | 47900 | 54300 |
| | Plasma | 42 | 1 | 0.0385 | 18.01 | 124 | 178 |
| | Spleen | 4980 | 1 | 0.044 | 15.77 | 63100 | 70700 |
| Test Formulation | Brain | 14.1 | 2 | NC | NC | 78.2 | NC |
| | Heart | 2360 | 1 | 0.0545 | 12.71 | 27900 | 30000 |
| | Kidney | 8140 | 1 | 0.0495 | 14.01 | 81700 | 89200 |
| | Liver | 1790 | 1 | 0.0609 | 11.38 | 7990 | 8300 |
| | Lungs | 5390 | 1 | 0.0452 | 15.33 | 56200 | 62700 |
| | Plasma | 63.5 | 1 | 0.0705 | 9.83 | 153 | 174 |
| | Spleen | 4360 | 1 | 0.0494 | 14.03 | 60000 | 66100 |

| Treatment | Tissue | $AUC_{0-24\ hr}$ (hr*ng/mL or hr*ng/g) | $AUC_{last}$ Tissue/ Plasma ratio | $V_{ss\_obs}$ (L/kg) | $V_{z\_obs}$ (L/kg) | $Cl\_{obs}$ (mL/min/kg) |
|---|---|---|---|---|---|---|
| JEVTANA ® | Brain | 74.7 | 0.505 | 59.1 | 55.9 | 310 |
| | Heart | 18600 | 191 | 0.803 | 1 | 0.807 |
| | Kidney | 59500 | 598 | 0.259 | 0.324 | 0.254 |
| | Liver | 5780 | 54.8 | 2.21 | 3.53 | 2.87 |
| | Lungs | 37700 | 386 | 0.437 | 0.559 | 0.384 |
| | Plasma | 124 | — | 135 | 182 | 117 |
| | Spleen | 47900 | 509 | 0.338 | 0.402 | 0.295 |
| Test Formulation | Brain | 104 | 0.511 | NC | NC | NC |
| | Heart | 22500 | 182 | 0.639 | 0.764 | 0.694 |
| | Kidney | 66700 | 534 | 0.222 | 0.283 | 0.234 |
| | Liver | 6940 | 52.2 | 1.57 | 2.47 | 2.51 |
| | Lungs | 44900 | 367 | 0.352 | 0.441 | 0.332 |
| | Plasma | 153 | — | 60.7 | 102 | 120 |
| | Spleen | 47800 | 392 | 0.326 | 0.383 | 0.315 |

Note:
NC = Not calculated due to insufficient concentrations; Plasma pharmacokinetic parameters were considered as Cmax = ng/mL and AUC = ng*hr/mL. Whereas for tissues pharmacokinetic parameters were considered as Cmax = ng/g and AUC = ng*hr/g.

Results

Study 4

Objective: To evaluate the comparative anticancer potential of ready to dilute formulation of cabazitaxel in xenograft mouse model Method and Material

| Test System | Nude Mouse (*Mus musculus*) Foxn-1 nu/nu strain |
|---|---|
| Sex | Female |
| Rationale | To evaluate the comparative anticancer potential of JEVTANA ® (Cabazitaxel Reference Listed Drug) and Cabazitaxel Ready to dilute formulation (Cipla Ltd.) in DU145 prostate cancer xenograft model in nude mice |
| Source of animals | Charles River Laboratories USA |
| Total no of animals | 34 |
| Age at study/Body Weight | 7-8 weeks/18.6 to 23.5 g (with in ±20% of mean). |
| Veterinary Examination | Prior to the final assignment to the study, mice will be subjected to veterinary examination to ensure that the selected mice are in a good state of health |
| Test System | Nude Mouse (*Mus musculus*) Foxn-1 nu/nu strain |
| Animal Identification | Animals will be uniquely identified by ear punching and also by body marking with permanent marker and cage label. |
| Acclimatization | Animals were acclimatize as per standard protocol |
| Feed and Water | Animals were given an autoclaved commercial diet (Nutrilab Rodent Feed) and autoclaved water ad libitum. |
| Animal handling | Experiment will be carried out by qualified & trained scientific personnel's (trained in animal handling, drug administration and experimentation). |

Test Item: JEVTANA® (Injection/& 40 mg/mL) and Test Cabazitaxel Formulation

JEVTANA® solution as well as Test Formulation were prepared using method as covered under study 1.

Route of administration: bolus intravenous administration within 1 minute.

Intravenous Infusion: Infusion system includes a swivel (Instech, USA), tubing (Co-ex infusion tubing), syringes and an infusion pump (Pico plus -Harvard apparatus). Each rat was administered at a 12 mg/kg dose level of Cabazitaxel (JEVTANA®) or Cabazitaxel RTD (Cipla) by bolus intravenous administration within one minute. Formulation strength required for infusion is 0.24 mg/mL.

| Group | Animal ID No. | Dose |
|---|---|---|
| G1 Vehicle Control | 1-10 | 5 w/v % dextrose solution |
| G2 Test Formulation | 11-22 | 12 mg/kg |
| G3 (JEVTANA®) | 23-34 | 12 mg/kg |

In-Life Observation and Measurements

| | |
|---|---|
| Data Acquisition | Each animal's number was recorded manually by checking the ear marking. All tumor volume measurements were acquired with digital caliper (Mitutoyo Corp., Japan). |
| Mortality | Mortality checks were performed daily during the study |
| Clinical Observations | Animals were monitored for clinical signs (such as illness and behavioral changes once every-day throughout the study |
| Body Weight | Body weight was recorded for all animals on days, 1, 3, 5, 8, 10, 15, 17, and 19 |
| Tumor Measurements | Tumor dimensions (length and breadth) were measured for all animals on days 1, 3, 5, 8, 10, 15, 17, and 19. Tumor volumes were calculated using the formula $(b^2 \ast 1) \ast 0.52$ where $1$ = length, $b$ = breadth. Tumor growth inhibition was calculated after normalizing the tumor volume on a given day to that on day 1. |

Plasma and Tumor pharmacokinetics: On the day of experiment termination (day 19), ~0.25 mL blood was collected from retro-orbital sinus using a fine capillary tube. The blood samples were immediately placed on ice following which plasma was separated by centrifuging under 4000 rpm at 2-8° C. for 10 min. Plasma was separated and stored at −70° C. until bioanalysis

| | Blood and tumor harvesting timepoints/ Animal ID No. | | | |
|---|---|---|---|---|
| Group | 1 hr | 2 hr | 3 hr | 4 hr |
| 1 Vehicle Control | — | — | — | — |
| 2 Cabazitaxel RTD (Cipla) | RTD 1-3 | RTD 4-6 | RTD 7-9 | RTD 10-12 |
| 3 Cabazitaxel (JEVTANA®) RLD | RLD 1-3 | RLD 4-6 | RLD 7-9 | RLD 10-12 |

At the end of blood collection, animals were humanely euthanized by cervical dislocation and tumor in toto was harvested from all the animals, transferred to pre-labeled microcentrifuge tubes before flash freezing in liquid nitrogen. After flash freezing, tubes were transferred to a deep freezer at −70° C. till bioanalysis for cabazitaxel.

Procedure: Human prostate cancer cell line, DU145 cell line was sourced from American Type Culture Collection (ATCC), USA. DU145 cells (5×106) at their exponential growth phase were inoculated subcutaneously on the dorsal right flank in athymic female mice.

When the xenografts had grown to a size of ~90 mm3 (approximately 2-3 weeks post cell injection), animals were treated with either test formulation or RLD formulation at 12 mg/kg mouse body weight on days 1, 7, 13, and 19 intravenously. Animals in the vehicle control group received 5 w/v % dextrose solution. Growth of prostate xenografts (tumor volume) and whole body weights were recorded twice weekly (on days 1, 3, 5, 8, 10, 15, 17, 19) during treatment period. Animals were also monitored for clinical signs and mortality everyday throughout the study. On the day of sacrifice (day 19), blood and tumors were collected from set of animals (4 animals in each time point) at stipulated time points (1, 2, 3, and 4 h post-dose). At the end of blood collection, animals were humanely euthanized by cervical dislocation and tumor in toto was harvested from all the animals, transferred to pre-labeled microcentrifuge tubes before flash freezing in liquid nitrogen. After flash freezing, tubes were transferred to a deep freezer at −70° C. till bioanalysis of cabazitaxel.

Bioanalysis: The concentrations of Cabazitaxel in plasma and tumor tissue were determined using a qualified LC-MS/MS method. Pharmacokinetic parameters were determined by using standard non-compartmental analysis (Phoenix WinNonLin® 6.4, Pharsight Corporation, Mountain View, Calif. 94040/USA) using linear trapezoidal with linear interpolation method.

Pharmacokinetic data analysis and Evaluation: Phoenix® Software, version 6.4, USA was used for studying Pharmacokinetic parameters such as Cmax, Tmax, Kel, T½, AUC (0-t), AUC (0-∞), VD, Geometric means, 90 percent Confidence intervals (CI). Bioequivalence will be calculated for Reference (JEVTANA®) Vs Cipla formulation using linear trapezoidal with linear interpolation method. For all biological matrixes the pharmacokinetic parameters were calculated. The data was analysed and interpreted both biologically and statistically. T-test was applied for the group comparison.

Results: Cabazitaxel was well tolerated in both treatment groups and no mortality was observed. No treatment related clinical signs were also observed in the study. Body weight of mice in test and RLD formulations treated groups were comparable and there was no statistically significant difference in body weight gain between these groups. Growth of DU145 xenografts in vehicle control group had normal progression with the average tumor volume reaching up to 489 mm3. A significant inhibition of xenograft growth was obtained for both test and RLD formulations whose tumor volumes were 110 mm3 (p<0.0001) and 77 mm3 (p<0.0001), respectively in comparison to vehicle control. The calculated tumor growth inhibition (TGI) for test formulation and RLD formulation on the day of experimental termination (day 19) were 95% and 103%, respectively. The results suggest that Cabazitaxel exposures both in plasma and tissues tested were found to be comparable among RLD and test formulations

TABLE 7

Group mean body weight SEM (g) of animals.

| | Mean ± | Body weight (g) on days | | | | | | | | |
|---|---|---|---|---|---|---|---|---|---|---|
| | SEM | 1 | 3 | 5 | 8 | 10 | 12 | 15 | 17 | 19 |
| Vehicle Control | Mean | 21.4 | 22.5 | 23.5 | 25.2 | 25.5 | 25.4 | 25.7 | 25.2 | 25.8 |
| | SEM | 0.4 | 0.3 | 0.4 | 0.4 | 0.4 | 0.5 | 0.4 | 0.4 | 0.4 |

TABLE 7-continued

Group mean body weight SEM (g) of animals.

| Mean ± | | Body weight (g) on days | | | | | | | |
|---|---|---|---|---|---|---|---|---|---|
| | SEM | 1 | 3 | 5 | 8 | 10 | 12 | 15 | 17 | 19 |
| Test formulation: (12 mg/kg; IV) | Mean | 21.3 | 21.6 | 21.4 | 22.5 | 22.4 | 22.4 | 22.4 | 21.7 | 23.2 |
| | SEM | 0.3 | 0.4 | 0.3 | 0.4 | 0.3 | 0.3 | 0.4 | 0.4 | 0.5 |
| JEVTANA ® (12 mg/kg; IV) | Mean | 21.3 | 21.6 | 21.8 | 22.4 | 22.1 | 21.6 | 21.2 | 20.7 | 21.8 |
| | SEM | 03 | 0.3 | 0.3 | 0.3 | 0.4 | 0.5 | 0.5 | 0.6 | 0.6 |

TABLE 8

Tumor volume ± SEM (mm3) of animals

| | | Tumor Volume (mm$^3$) on day | | | | | | | |
|---|---|---|---|---|---|---|---|---|---|
| | — | 1 | 3 | 5 | 8 | 10 | 15 | 17 | 19 |
| Vehicle Control | Mean | 93.84 | 151.43 | 186.83 | 240.64 | 295.04 | 368.64 | 423.44 | 489.18 |
| | SEM | 3.27 | 5.29 | 5.31 | 9.05 | 14.15 | 26.68 | 25.79 | 30.94 |
| Test formulation: (12 mg/kg; IV) | Mean | 90.31 | 112.18 | 118.74 | 124.14 | 116.30 | 109.44 | 100.07 | 109.81 |
| | SEM | 3.75 | 8.31 | 7.26 | 11.48 | 12.53 | 13.92 | 13.69 | 12.15 |
| JEVTANA ® (12 mg/kg; IV) | Mean | 89.98 | 114.07 | 124.08 | 124.21 | 117.25 | 78.06 | 70.12 | 77.24 |
| | SEM | 3.92 | 9.90 | 13.55 | 15.03 | 15.68 | 10.20 | 9.51 | 10.29 |

TABLE 9

Percent tumor growth inhibition

| | % Tumor Growth inhibition (% TGI) by Delta TV | | | | | | | |
|---|---|---|---|---|---|---|---|---|
| Treatment | 1 | 3 | 5 | 8 | 10 | 15 | 17 | 19 |
| Test formulation (12 mg/kg; IV) | — | 62.03 | 69.43 | 76.96 | 87.08 | 93.04 | 97.04 | 95.07 |
| JEVTANA ® (12 mg/kg; IV) | — | 58.16 | 63.32 | 76.68 | 86.45 | 104.34 | 106.02 | 103.22 |

TABLE 10

Cabazitaxel pharmacokinetics parameters

| | Plasma | | Tumor | |
|---|---|---|---|---|
| PK Parameters | Test Formulation | JEVTANA ® | Test Formulation | JEVTANA ® |
| AUC-last (h*ng/mL) | 1437 | 1707 | 25408 | 24714 |
| C-max (ng/mL) | 594 | 666 | 7074 | 6625 |

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method of treating cancer in a patient in need thereof, comprising administering composition comprising an effective amount of a compound having the formula:

or a pharmaceutically acceptable salt thereof and at least one solubilizer wherein:
a) the solubilizer comprises a compound of the formula wherein x is an integer from 1-20; $y^1$ is an integer from 2-20; $z^1$ is an integer from 1-15; and $Z^1$ is selected from hydrogen or the group OR, in which R is selected from hydrogen and a group having the formula:

wherein y2 is an integer from 2-20; $z^2$ is an integer from 1-15; and $Z^2$ is selected from hydrogen or hydroxyl, or
b) the solubilizer comprises compound of the formula wherein $x^2$ is an integer from 1-20; wherein $y^3$ is an integer from 1-20; $z^3$ is an integer from 0-15;
$Z^3$ is selected from hydroxyl and hydrogen, and $Z^4$ is selected from hydroxyl and the group having the formula:

wherein $y^4$ is an integer from 1-20; $z^4$ is an integer from 0-15; and $Z^5$ is selected from hydrogen or hydroxyl
wherein the composition is a solution and does not include Cremopher EL; and
wherein the composition is administered by parenteral injection.

2. The method according to claim 1, wherein the solubilizer comprises a macrogol 18-hydroxy stearate.

3. The method according to claim 1, wherein the solubilizer comprises a caprylocaproyl polyoxylglyceride.

4. The method according to claim 1, wherein the composition comprises a surfactant.

5. The method according to claim 1, wherein the surfactant comprises a polyethylene oxide.

6. The method according to claim 1, wherein the composition further comprises at least one alcohol, at least one acid, and at least one solvent.

7. The method according to claim 1, wherein the composition is administered by intravenous injection.

8. The method according to claim 1, wherein the compound is administered at a dose of 25 mg/m$^2$ once every three weeks.

9. The method according to claim 1, wherein the cancer comprises hormone-refractory metastatic prostate cancer.

10. The method according to claim 1, wherein the solubilizer is present in an amount from 5-50% by weight of the total composition.

11. The method according to claim 4, wherein the surfactant is present in an amount from 5-45% by weight of the total composition.

12. The method according to claim 6, wherein the alcohol comprises ethanol, benzyl alcohol, tertiary-butyl alcohol, isopropyl alcohol, or a mixture thereof.

13. The method according to claim 12, wherein the alcohol comprises ethanol.

14. The method according to claim 6, wherein the acid comprises citric acid, tartaric acid, acetic acid and mixtures thereof.

15. The method according to claim 6, wherein the acid is present in an amount from about 0.1-1.0% of the total weight of the composition.

16. The method according to claim 15, wherein the acid comprises citric acid.

17. The method according to claim 6, wherein the solvent comprises diethylene glycol monoethyl ether, dimethylacetamide, dimethylsulfoxide, propylene glycol or glycofurol.

18. The method according to claim 17, wherein the solvent is present in an amount of about 0.1-10% of the total weight of the composition.

19. The method according to claim 1, wherein the composition comprises albumin and water.